`US008003332B2`

(12) United States Patent
Kielian et al.

(10) Patent No.: US 8,003,332 B2
(45) Date of Patent: Aug. 23, 2011

(54) INHIBITION OF MEMBRANE FUSION PROTEINS

(75) Inventors

FIG. 4 liposomes, low pH, solubilization

E ectodomain monomer (virus or expressed)

detergent-solubilized E trimer

Target 1 liposomes, low pH, solubilization

E dI/dII monomer detergent-solubilized E dI/dII trimer

Target 2

FIG. 6C

|              | Calculated mass (Da) | Measured mass (Da) | Difference (Da) |
|--------------|----------------------|--------------------|-----------------|
| DIII         | 9664.9               | 9659               | 5.9             |
| DIIIS        | 12832.5              | 12828              | 4.5             |
| His-DIII     | 13663.1              | 13657              | 6.1             |
| His-DIIIS    | 16830.7              | 16825              | 5.7             |
| DV2DIIIH1    | 13339.6              | 13337              | 2.6             |
| His-DV2DIII  | 15292.4              | 15289              | 3.4             |

INHIBITION OF MEMBRANE FUSION PROTEINS

CROSS-REFERENCE TO RELATED APPLICATION

This is a U.S. national phase of PCT Application No. PCT/US2006/017284, filed May 4, 2006, which claims the benefit of U.S. Provisional Application No. 60/678,467, filed May 6, 2005.

STATEMENT REGARDING FEDERALLY SPONSORED RESEARCH OR DEVELOPMENT

This invention was made with government support under grant number GM52929 awarded by the National Institutes of Health. The government has certain rights in the invention.

BACKGROUND OF THE INVENTION (1) Field of the Invention

The present invention generally relates to control of viral infection. More specifically, the invention is directed to control of virus-membrane fusion reactions of viruses having class II fusion proteins, and methods for identifying compounds that effect that control.

(2) Description of the Related Art

REFERENCES CITED

Ahn, A., Klimjack, M. R., Chatterjee, P. K., and Kielian, M. (1999). An epitope of the Semliki Forest virus fusion protein exposed during virus-membrane fusion. J. Virol. 73, 10029-10039.

Ahn, A., Gibbons, D. L., and Kielian, M. (2002). The fusion peptide of Semliki Forest virus associates with sterol-rich membrane domains. J. Virol. 76, 3267-3275.

Allison, S. L., Schalish, J., Stiasny, K., Mandl, C. W., Kunz, C., and Heinz, F. X. (1995). Oligomeric rearrangement of tick-borne encephalitis virus envelope proteins induced by an acidic pH. J. Virol. 69, 695-700.

Baker, K. A., Dutch, R. E., Lamb, R. A., and Jardetzky, T. S. (1999). Structural basis for paramyxovirus-mediated membrane fusion. Mol. Cell 3, 309-319.

Binley, J., and Moore, J. P. (1997). HIV-cell fusion: The viral mousetrap. Nature 387, 346-348.

Boger, D. L., Desharnais, J., and Capps, K. (2003). Solution-phase combinatorial libraries: modulating cellular signaling by targeting protein-protein or protein-DNA interactions. Angew Chem Int Ed Engl 42, 4138-76.

Bressanelli, S., Stiasny, K., Allison, S. L., Stura, E. A., Duquerroy, S., Lescar, J., Heinz, F. X., and Rey, F. A. (2004). Structure of a flavivirus envelope glycoprotein in its low-pH-induced membrane fusion conformation. EMBO J. 23, 728-38.

Chan, D. C., Fass, D., Berger, J. M., and Kim, P. S. (1997). Core structure of gp41 from the HIV envelope glycoprotein. Cell 89, 263-273.

Chatterjee, P. K., et al. (2002). Novel mutations that control the sphingolipid and cholesterol dependence of the Semliki Forest virus fusion protein. J. Virol. 76, 12712-22.

Cianci, C., Langley, D. R., Dischino, D. D., Sun, Y., Yu, K. L., Stanley, A., Roach, J., Li, Z., Dalterio, R., Colonno, R., Meanwell, N. A., and Krystal, M. (2004). Targeting a binding pocket within the trimer-of-hairpins: small-molecule inhibition of viral fusion. Proc. Natl. Acad. Sci. USA 101, 15046-51.

Clarke, T. (2002). Dengue virus: break-bone fever. Nature 416, 672-4.

Corver, J., Ortiz, A., Allison, S. L., Schalich, J., Heinz, F. X., and Wilschut, J. (2000). Membrane fusion activity of tick-borne encephalitis virus and recombinant subviral particles in a liposomal model system. Virol. 269, 37-46.

Dutch, R. E., Jardetzky, T. S., and Lamb, R. A. (2000). Virus membrane fusion proteins: biological machines that undergo a metamorphosis. Biosci Rep 20, 597-612.

Eckert, D. M., and Kim, P. S. (2001a). Design of potent inhibitors of HIV-1 entry from the gp41 N-peptide region. Proc. Natl. Acad. Sci. USA 98, 11187-92.

Eckert, D. M., and Kim, P. S. (2001b). Mechanisms of viral membrane fusion and its inhibition. Annu. Rev. Biochem. 70, 777-810.

Fass, D., Harrison, S. C., and Kim, P. S. (1996). Structure of Moloney murine virus envelope domain at 1.7 A resolution. Nature Struct. Biol. 3, 465-469.

Feng, Y., Broder, C. C., Kennedy, P. E., and Berger, E. A. (1996). HIV-1 entry cofactor: functional cDNA cloning of a seven-transmembrane, G protein-coupled receptor. Science 272, 872-877.

Garoff, H., Hewson, R., and Opstelten, D.-J. E. (1998). Virus maturation by budding. Microbiol. and Mol. Biol. Rev. 62, 1171-1190.

Garoff, H., Sjoberg, M., and Cheng, R. H. (2004). Budding of alphaviruses. Virus Res 106, 103-16.

Garry, C. E., and Garry, R. F. (2004). Proteomics computational analyses suggest that the carboxyl terminal glycoproteins of Bunyaviruses are class II viral fusion protein (beta-penetrenes). Theor. Biol. Med. Modelling 1, 10-26.

Gibbons, D. L., and Kielian, M. (2002). Molecular dissection of the Semliki Forest virus homotrimer reveals two functionally distinct regions of the fusion protein. J. Virol. 76, 1194-1205.

Gibbons, D. L., Erk, I., Reilly, B., Navaza, J., Kielian, M., Rey, F. A., and Lepault, J. (2003). Visualization of the target-membrane-inserted fusion protein of Semliki Forest virus by combined electron microscopy and crystallography. Cell 114, 573-583.

Gibbons, D. L., Reilly, B., Ahn, A., Vaney, M.-C., Vigouroux, A., Rey, F. A., and Kielian, M. (2004a). Purification and crystallization reveal two types of interactions of the fusion protein homotrimer of Semliki Forest virus. J. Virol. 787, 3514-3523.

Gibbons, D. L., Vaney, M.-C., Roussel, A., Vigouroux, A., Reilly, B., Lepault, J., Kielian, M., and Rey, F. A. (2004b). Conformational change and protein-protein interactions of the fusion protein of Semliki Forest virus. Nature 427, 320-325.

Glomb-Reinmund, S., and Kielian, M. (1998). The role of low pH and disulfide shuffling in the entry and fusion of Semliki Forest virus and Sindbis virus. Virol. 248, 372-381.

Griffin, D. E. (1986). Alphavirus pathogenesis and immunity. In "The Togaviridae and Flaviviridae" (S. Sclilesinger, and M. J. Schlesinger, Eds.), pp. 209-249. Plenum Press, New York.

Gubler, D. J. (1998). Dengue and dengue hemorrhagic fever. Clin. Microbiol. Rev. 11, 480-496.

Heinz, F. X., Stiasny, K., Puschner-Auer, G., Holzmann, H., Allison, S. L., Mandl, C. W., and Kunz, C. (1994). Structural changes and functional control of the tick-borne encephalitis virus glycoprotein E by the heterodimeric association with protein prM. Virol. 198, 109-117.

Heinz, F. X., and Allison, S. L. (2001). The machinery for flavivirus fusion with host cell membranes. Curr Opin Microbiol 4, 450-5.

Hernandez, L. D., Peters, R. J., Delos, S. E., Young, J. A. T., Agard, D. A., and White, J. M. (1997). Activation of a retroviral membrane fusion protein: Soluble receptor-induced liposome binding of the ALSV envelope glycoprotein. J. Cell Biol. 139, 1455-1464.

Hilgard, P., and Stockert, R. (2000). Heparan sulfate proteoglycans initiate dengue virus infection of hepatocytes. Hepatology 32, 1069-77.

Hung, J. J., Hsieh, M. T., Young, M. J., Kao, C. L., King, C. C., and Chang, W. (2004). An external loop region of domain III of dengue virus type 2 envelope protein is involved in serotype-specific binding to mosquito but not mammalian cells. J. Virol. 78, 378-88.

Jaiswal, S., Khanna, N., and Swaminathan, S. (2004). High-level expression and one-step purification of recombinant dengue virus type 2 envelope domain III protein in *Escherichia coli*. Protein Expr Purif 33, 80-91.

Kieber-Emmons et al. (1997) Curr. Opin. Biotechnol. 8, 435-441.

Kielian, M. (1995). Membrane fusion and the alphavirus life cycle. Adv. Virus Res. 45, 113-151.

Kielian, M. (2006) "Class II virus-membrane fusion proteins". Virol. 344:38-47.

Kielian, M. C., and Helenius, A. (1984). The role of cholesterol in the fusion of Semliki Forest virus with membranes. J. Virol. 52, 281-283.

Kielian, M., and Helenius, A. (1985). pH-induced alterations in the fusogenic spike protein of Semliki Forest Virus. J. Cell Biol. 101, 2284-2291.

Kielian, M. and Ray, F. A. (2006). Virus membrane-fusion proteins: more than one way to make a hairpin. Nat. Rev. Microbiol. 4, 67-76.

Kielian, M., Klimjack, M. R., Ghosh, S., and Duffus, W. A. (1996). Mechanisms of mutations inhibiting fusion and infection by Semliki Forest virus. J. Cell Biol. 134, 863-872.

Kielian, M., Chatterjee, P. K., Gibbons, D. L., and Lu, Y. E. (2000). Specific roles for lipids in virus fusion and exit: Examples from the alphaviruses. In "Subcellular Biochemistry Vol. 34. Fusion of Biological Membranes and Related Problems." (H. Hilderson, and S. Fuller, Eds.), pp. 409-455. Plenum Publishers, New York.

Klimjack, M. R., Jeffrey, S., and Kielian, M. (1994). Membrane and protein interactions of a soluble form of the Semliki Forest virus fusion protein. J. Virol. 68, 6940-6946.

Lakowicz, J. R. (1999). "Principles of Fluorescence Spectroscopy." Kluwer Academic/Plenum Press, New York.

Lescar, J., Roussel, A., Wien, M. W., Navaza, J., Fuller, S. D., Wengler, G., and Rey, F. A. (2001). The fusion glycoprotein shell of Semliki Forest virus: an icosahedral assembly primed for fusogenic activation at endosomal pH. Cell 105, 137-48.

Liao, M. and Kielian, M. (2006). Domain III from class II fusion proteins functions as a dominant-negative inhibitor of virus membrane fusion. J. Cell Biol. 171, 111-120.

Lindenbach, B. D., and Rice, C. M. (2001). Flaviviridae: the viruses and their replication. 4 ed. In "Field's Virology" (D. M. Knipe, and P. M. Howley, Eds.), pp. 991-1041. Lippincott, Williams and Wilkins, Philadelphia, Pa.

Lu, Y. E., Cassese, T., and Kielian, M. (1999). The cholesterol requirement for Sindbis virus entry and exit and characterization of a spike protein region involved in cholesterol dependence. J. Virol. 73, 4272-4278.

Malashkevich, V. N., Schneider, B. J., McNally, M. L., Milhollen, M. A., Pang, J. X., and Kim, P. S. (1999). Core structure of the envelope glycoprotein GP2 from Ebola virus at 1.9-Å resolution. Proc. Natl. Acad. Sci. USA 96, 2662-2667.

Matlin, K. S., Reggio, H., Helenius, A., and Simons, K. (1982). Pathway of Vesicular Stomatitis virus entry leading to infection. J. Mol. Biol. 156, 609-631.

Melikyan, G. B., Markosyan, R. M., Hemmati, H., Delmedico, M. K., Lambert, D. M., and Cohen, F. S. (2000). Evidence that the transition of HIV-1 gp41 into a six-helix bundle, not the bundle configuration, induces membrane fusion. J. Cell Biol. 151, 413-423.

Memon, M. I., and Memon, M. A. (2002). Hepatitis C: an epidemiological review. J Viral Hepat 9, 84-100.

MMWR (1992). Arboviral diseases—United States, 1991. Morb. Mort. Wk. Rep. 41, 545-548.

MMWR (1994). Arbovirus disease—United States, 1993. Morb. Mort. Wk. Rep. 43, 385-387.

Modis, Y., Ogata, S., Clements, D., and Harrison, S. C. (2003). A ligand-binding pocket in the dengue virus envelope glycoprotein. Proc. Natl. Acad. Sci. USA 100, 6986-91.

Modis, Y., Ogata, S., Clements, D., and Harrison, S. C. (2004). Structure of the dengue virus envelope protein after membrane fusion. Nature 427, 313-9.

Modis et al, (2005) J. Virology, 79:1223-31.

Monath, T. P. (1994). Dengue: the risk to developed and developing countries. Proc. Natl. Acad. Sci. USA 91, 2395-400.

Moore, J. P., and Doms, R. W. (2003). The entry of entry inhibitors: A fusion of science and medicine. Proc. Natl. Acad. Sci. USA 100, 10598-602.

Morrison, T. G. (2001). The three faces of paramyxovirus attachment proteins. Trends in Microbiol. 9, 103-5.

Mothes, W., Boerger, A. L., Narayan, S., Cunningham, J. M., and Young, J. A. (2000). Retroviral entry mediated by receptor priming and low pH triggering of an envelope glycoprotein. Cell 103, 679-89.

Owicki, J. C. (2000). Fluorescence polarization and anisotropy in high throughput screening: perspectives and primer. J. Biomol. Screen. 5, 297-306.

Phalen, T., and Kielian, M. (1991). Cholesterol is required for infection by Semliki Forest virus. J. Cell Biol. 112, 615-623.

Pletnev, S. V., Zhang, W., Mukhopadhyay, S., Fisher, B. R., Hernandez, R., Brown, D. T., Baker, T. S., Rossmann, M. G., and Kuhn, R. J. (2001). Locations of carbohydrate sites on alphavirus glycoproteins show that E1 forms an icosahedral scaffold. Cell 105, 127-36.

Rey, F. A., Heinz, F. X., Mandl, C., Kunz, C., and Harrison, S. C. (1995). The envelope glycoprotein from tick-borne encephalitis virus at 2 A resolution. Nature 375, 291-298.

Ripka et al. (1998) Curr. Opin. Chem. Biol. 2, 441-452.

Rothman, A. L., and Ennis, F. A. (1999). Immunopathogenesis of Dengue hemorrhagic fever. Virol. 257, 1-6.

Roussel, A. et al. (2006). Structure and interactions at the viral surface of the envelope protein E1 of Semliki Forest Virus. Structure 14, 75-86.

Russell, C. J., Jardetzky, T. S., and Lamb, R. A. (2001). Membrane fusion machines of paramyxoviruses: capture of intermediates of fusion. EMBO J. 20, 4024-34.

Salminen, A., Wahlberg, J. M., Lobigs, M., Liljeström, P., and Garoff, H. (1992). Membrane fusion process of Semliki Forest virus II: Cleavage-dependent reorganization of the spike protein complex controls virus entry. J. Cell Biol. 116, 349-357.

Sanderson (1999) Med. Res. Rev. 19, 179-197.

Schlesinger, S., and Schlesinger, M. J. (2001). Togaviridae: the viruses and their replication. In "Fields Virology" (D. M. Knipe, and P. M. Howley, Eds.), pp. 895-916. Lippincott, Williams and Wilkins, Philadelphia.

Scopes, R. K. (1974). Measurement of protein by spectrophotometry at 205 nm. Anal. Biochem. 59, 277-282.

Sieczkarski, S. B., and Whittaker, G. R. (2002). Influenza virus can enter and infect cells in the absence of clathrin-mediated endocytosis. J. Virol. 76, 10455-64.

Sieczkarski, S. B., and Whittaker, G. R. (2003). Differential requirements of Rab5 and Rab7 for endocytosis of influenza and other enveloped viruses. Traffic 4, 333-43.

Skehel, J. J., and Wiley, D. C. (2000). Receptor binding and membrane fusion in virus entry: The influenza hemagglutinin. Annu. Rev. Biochem. 69, 531-569.

Smit, J. M., Bittman, R., and Wilschut, J. (1999). Low-pH-dependent fusion of sindbis virus with receptor-free cholesterol- and sphingolipid-containing liposomes. J. Virol. 73, 8476-8484.

Stiasny, K., Allison, S. L., Schalich, J., and Heinz, F. X. (2002). Membrane interactions of the tick-borne encephalitis virus fusion protein E at low pH. J. Virol. 76, 3784-90.

Stiasny, K., Koessl, C., and Heinz, F. X. (2003). Involvement of lipids in different steps of the flavivirus fusion mechanism. J. Virol. 77, 7856-62.

Stiasny, K., Bressanelli, S., Lepault, J., Rey, F. A., and Heinz, F. X. (2004). Characterization of a membrane-associated trimeric low-pH-induced Form of the class II viral fusion protein E from tick-borne encephalitis virus and its crystallization. J. Virol. 78, 3178-83.

Strauss, J. H., and Strauss, E. G. (1994). The alphaviruses: gene expression, replication, and evolution. Microbiol. Rev. 58, 491-562.

Strauss, J. H., Strauss, E. G., and Kuhn, R. J. (1995). Budding of alphaviruses. Trends in Microbiol. 3, 346-350.

Supekar, V. M., Bruckmann, C., Ingallinella, P., Bianchi, E., Pessi, A., and Carfi, A. (2004). Structure of a proteolytically resistant core from the severe acute respiratory syndrome coronavirus S2 fusion protein. Proc. Natl. Acad. Sci. USA 101, 17958-63.

Vashishtha, M., Phalen, T., Marquardt, M. T., Ryu, J. S., Ng, A. C., and Kielian, M. (1998). A single point mutation controls the cholesterol dependence of Semliki Forest virus entry and exit. J. Cell Biol. 140, 91-99.

Volk, D. E., Beasley, D. W., Kallick, D. A., Holbrook, M. R., Barrett, A. D., and Gorenstein, D. G. (2004). Solution structure and antibody binding studies of the envelope protein domain III from the New York strain of West Nile virus. J. Biol. Chem. 279, 38755-61.

Wahlberg, J. M., and Garoff, H. (1992). Membrane fusion process of Semliki Forest virus I: Low pH-induced rearrangement in spike protein quaternary structure precedes virus penetration into cells. J. Cell Biol. 116, 339-348.

Weaver, S. C., and Barrett, A. D. (2004). Transmission cycles, host range, evolution and emergence of arboviral disease. Nat Rev Microbiol 2, 789-801.

Weaver, S. C., Ferro, C., Barrera, R., Boshell, J., and Navarro, J. C. (2004). Venezuelan equine encephalitis. Annu Rev Entomol 49, 141-74.

Weissenhom, W., Dessen, A., Harrison, S. C., Skehel, J. J., and Wiley, D. C. (1997). Atomic structure of the ectodomain from HIV-1 gp41. Nature 387, 426-430.

Weissenhom, W., Dessen, A., Calder, L. J., Harrison, S. C., Skehel, J. J., and Wiley, D. C. (1999). Structural basis for membrane fusion by enveloped viruses. Mol. Membrane Biol. 16, 3-9.

WHO (2002). Dengue and Dengue Haemorrhagic Fever. WHO Fact Sheet N. 117.

Wu, K. P., Wu, C. W., Tsao, Y. P., Kuo, T. W., Lou, Y. C., Lin, C. W., Wu, S. C., and Cheng, J. W. (2003). Structural basis of a flavivirus recognized by its neutralizing antibody: solution structure of the domain III of the Japanese encephalitis virus envelope protein. J. Biol. Chem. 278, 46007-13.

Yagnik, A. T., Lahm, A., Meola, A., Roccasecca, R. M., Ercole, B. B., Nicosia, A., and Tramontano, A. (2000). A model for the hepatitis C virus envelope glycoprotein E2. Proteins 40, 355-66.

Zaitseva, E. et al. (2005). Class II fusion protein of alphaviruses drives membrane fusion through the same pathway as class I proteins. J. Cell Biol. 169, 167-77.

Zhang, W., Mukhopadhyay, S., Pletnev, S. V., Baker, T. S., Kuhn, R. J., and Rossmann, M. G. (2002a). Placement of the structural proteins in sindbis virus. J. Virol. 76, 11645-58.

Zhang, W., Chipman, P. R., Corver, J., Johnson, P. R., Zhang, Y., Mukhopadhyay, S., Baker, T. S., Strauss, J. H., Rossmann, M. G., and Kuhn, R. J. (2003a). Visualization of membrane protein domains by cryo-electron microscopy of dengue virus. Nature Struct. Biol. 10, 907-12.

Zhang, X., Schwartz, J. C., Almo, S. C., and Nathenson, S. G. (2002b). Expression, refolding, purification, molecular characterization, crystallization, and preliminary X-ray analysis of the receptor binding domain of human B7-2. Protein Expr Purif 25, 105-13.

Zhang, X., Fugere, M., Day, R., and Kielian, M. (2003b). Furin processing and proteolytic activation of Semliki Forest virus. J. Virol. 77, 2981-9.

Zhang, Y., Corver, J., Chipman, P. R., Zhang, W., Pletnev, S. V., Sedlak, D., Baker, T. S., Strauss, J. H., Kuhn, R. J., and Rossmann, M. G. (2003c). Structures of immature flavivirus particles. EMBO J. 22, 2604-13.

Zhang, Y., Zhang, W., Ogata, S., Clements, D., Strauss, J. H., Baker, T. S., Kuhn, R. J., and Rossmann, M. G. (2004). Conformational changes of the flavivirus E glycoprotein. Structure (Camb) 12, 1607-18.

The role of flaviviruses and alphaviruses in disease. The flavivirus genus includes a number of serious human pathogens that are disseminated in nature by mosquito or tick vectors (Lindenbach and Rice, 2001). The flavivirus dengue virus is of particular concern as it has dramatically reemerged to become endemic in more than 100 countries including the US (Clarke, 2002; Gubler, 1998; Monath, 1994). Dengue is a major global health problem and the estimates are that more than one-third of the world's population lives in dengue fever endemic areas. The WHO estimates that there are ~100 million cases of dengue infection and 500,000 cases of the more lethal complication dengue hemorrhagic fever (DHF) per year, requiring 500,000 hospitalizations and causing ~25,000 deaths, mostly in children (WHO, 2002). This disease burden also has a significant economic impact in developing countries. Dengue virus is classified as a category A priority pathogen by the NIAID. While significant research on preventative vaccines is underway, it is complicated by the fact that antibodies can enhance infection leading to DHF and dengue shock syndrome (Rothman and Ennis, 1999). Control of the mosquito vector is the current mode of prevention but is itself problematic and almost nonexistent in many endemic countries (Weaver and Barrett, 2004). Thus, alternative antiviral strategies are sorely needed. Other important flavivirus pathogens include Japanese encephalitis (category B), the leading cause of viral encephalitis in Asia; tick-borne encephalitis virus (TBE) (category C), which causes thousands of cases of human illness yearly in northern and eastern Europe; and West Nile virus (category B), which has emerged recently as a human pathogen in Europe and North America. Although there has been a vaccine against yellow fever virus for many years, disease cases have increased to 200,000 per year with some 30,000 deaths, leading to the classification of this flavivirus as a category C emerging infectious disease. The Flaviviridae family also includes the more distantly related hepatitis C virus (HCV), an important blood-borne pathogen responsible for severe chronic liver disease and liver cancer (Memon and Memon, 2002).

The alphavirus genus contains ~24 virus species that are generally spread in nature by mosquito vectors (Schlesinger and Schlesinger, 2001; Strauss and Strauss, 1994). The alphaviruses eastern equine encephalitis (EEE) virus and western equine encephalitis (WEE) virus cause severe encephalitis in humans. Venezuelan equine encephalitis (VEE) virus causes encephalitis, myocarditis, pharyngitis, leukopenia, and hepatitis in humans, and leukopenia, encephalitis, and pancreatitis in horses (Griffin, 1986; Weaver et al., 2004). EEE virus is among the most virulent alphaviruses, with a case fatality rate of ~35% in humans of all age groups. Both EEE virus and WEE virus are endemic to the United States and responsible for periodic epidemics of encephalitis in humans (MMWR, 1992; MMWR, 1994). In the past, VEE was weaponized by both the US and the former USSR, and currently EEE, WEE, and VEE virus are all classified as category B priority pathogens. Given the known spread of mosquito vectors into new regions, these viruses are also potential emerging pathogens (Weaver and Barrett, 2004). There are no effective therapeutic drugs and, similar to flaviviruses, new antiviral strategies are very much needed. Semliki Forest virus (SFV) and Sindbis virus are highly developed experimental paradigms for the alphavirus genus in part because of their low pathogenicity in humans.

The Class I viral fusion proteins: structure and inhibition. Membrane fusion is a key step in the infection pathway of enveloped animal viruses. A number of virus membrane fusion proteins, exemplified by the influenza hemagglutinin (HA) and HIV gp41, share key features and are therefore grouped together as class I fusion proteins (reviewed in Dutch et al., 2000; Eckert and Kim, 2001b; Weissenhorn et al., 1999). Members of this class to date include orthomyxoviruses such as influenza (Skehel and Wiley, 2000), paramyxoviruses (Baker et al., 1999), retroviruses (Fass et al., 1996), filoviruses (Malashkevich et al., 1999), coronaviruses (Supekar et al., 2004) and human immunodeficiency virus-1 (HIV-1) (Chan et al., 1997; Weissenhorn et al., 1997). Fusion of viruses in this class may be triggered by low pH as in the case of influenza virus, by receptor interaction (Morrison, 2001), by receptor plus low pH (Hernandez et al., 1997; Mothes et al., 2000), or by receptor plus co-receptor interaction as in the case of HIV-1 (Binley and Moore, 1997; Feng et al., 1996). Class I fusion proteins are trimers that are generally proteolytically processed to produce a transmembrane polypeptide containing a hydrophobic sequence known as the fusion peptide. Once fusion is triggered the hydrophobic fusion peptide is translocated to the top of the molecule via formation of an extended trimeric coiled-coil α-helix (FIG. 1). The fusion peptide then inserts into the target membrane and the protein refolds to form a "trimer of hairpins" with a central α-helical coiled coil domain. Rearrangement to this hairpin configuration repositions the fusion peptide and transmembrane domains to the same end of a rod-like structure and drives the fusion reaction (Melikyan et al., 2000; Russell et al., 2001). Importantly, for a number of class I proteins, peptides containing sequences of the N or C-terminal interacting regions can bind to the fusion protein and inhibit fusion and infection by preventing refolding to the final hairpin conformation (reviewed in Eckert and Kim, 2001a; Moore and Doms, 2003). This dominant-negative approach is exemplified by the HIV peptide T20/Enfuvirtide, a licensed antiretroviral drug that corresponds to the C-terminal helix of gp41 (FIG. 1). While the first class I inhibitors were peptides, more recently small molecules that target critical sites of interaction in the trimer of hairpins have also been shown to act as fusion inhibitors. One such small molecule inhibitor of the paramyxovirus respiratory syncytial virus was recently demonstrated to bind to a hydrophobic pocket on the central coiled-coil of the fusion protein (Clanci et al., 2004). Thus, although they target only a subset of the contacts involved in forming the trimer of hairpins, small molecules can act as potent inhibitors of hairpin formation and fusion. As small molecules can have higher bioavailability than peptides, they provide an important approach to develop more widely useful fusion inhibitors, including the potential to target those viruses that fuse within endocytic compartments. Significantly, once the initial proof of principle was established by the HIV T20 studies, the inhibition of virus fusion became an important focus of antiviral research for other class I viruses.

Class II viral fusion proteins: the alphavirus/flavivirus class. The pre-fusion structures of the fusion protein ectodomains from the alphavirus Semliki Forest virus (SFV) (Lescar et al., 2001) and the flaviviruses dengue virus (Modis et al., 2003, 2005) and TBE virus (Rey et al., 1995) demonstrate that they are representative of a novel class of fusion proteins now termed "class II". The SFV fusion protein (termed E1) and those of the flaviviruses (termed E) are highly similar in overall fold and domain organization even though their primary sequences are not conserved (FIG. 2). Both E1 and E are elongated molecules containing three domains, with the fusion peptide (orange) at the tip of the molecule in domain II (yellow), and the stem region and transmembrane domain connecting to domain III (blue) at the opposite end. The structures are composed predominantly of β-strand secondary structure and contain no extended regions of α-helix or regions predicted to form coiled-coils. Electron cryo-microscopy of virus and fitting of the structures shows that the fusion proteins lie tangential (almost parallel) to the virus membrane and organize in an icosahedral scaffold (Lescar et al., 2001; Pletnev et al., 2001; Zhang et al., 2002a).

The alpha- and flavivirus membrane fusion reactions are induced by low pH within the endocytic pathway, which triggers the formation of a highly stable homotrimer (HT) of the fusion protein. All of the available evidence indicates that, analogous to formation of the class I hairpin, formation of the class II fusion protein HT is critical for the fusion reaction (Allison et al., 1995; Kielian et al., 1996; Wahlberg and Garoff, 1992). We developed methods to produce a proteolytically truncated ectodomain fragment of the SFV fusion protein E1 from purified virus (Gibbons and Kielian, 2002; Kielian and Helenius, 1985). We also developed a method to convert the soluble ectodomain, termed E1*, to the membrane-inserted homotrimer form by treatment of the protein at acid pH in the presence of cholesterol-containing liposomes (Klimjack et al., 1994). This E1* homotrimer was then solubilized, purified, crystallized and the homotrimer structure determined in collaboration with Dr. Félix Rey of the CNRS (Gibbons et al., 2004a; Gibbons et al., 2004b). Strikingly, during trimerization domain III (blue) and the stem region of E1* move about 37 Å towards the fusion peptide, and interact with the central core of the trimer (FIG. 3). Thus, although the E1* trimer does not contain an inner coiled-coil like the class I proteins, it forms a mechanistically similar "hairpin" structure: a highly stable protein rod with fusion peptide and transmembrane domains at the same end. The structures of the dengue virus and TBE homotrimers are remarkably similar to that of SFV (Bressanelli et al., 2004; Modis et al., 2004). Together the structural data demonstrate that the alphavirus and flavivirus membrane fusion proteins share common structural and functional features in both their pre-fusion and post-fusion conformations. Thus, the flaviviruses and alphaviruses form the inaugural members of the class II virus fusion proteins. We anticipate that, similar to the class I proteins, other viral fusion proteins will ultimately be assigned to class II as information about their structures becomes available. For example, modeling studies suggest that the HCV E2 protein may also be a class II virus fusion protein (Yagnik et al., 2000). Bunyaviridae also apparently has class II virus fusion proteins (Garry and Garry, 2004).

Life cycle of the alphaviruses and flaviviruses. Both the alphaviruses and flaviviruses are small spherical enveloped viruses containing plus-strand RNA genomes packaged with a capsid protein (reviewed in Lindenbach and Rice, 2001; Schlesinger and Schlesinger, 2001). The viral envelope contains the transmembrane fusion protein (E1 or E) and a second accessory or companion transmembrane protein (alphavirus E2 or flavivirus M). Both E2 and M are synthesized as larger precursor proteins (p62 and prM, respectively) that are cleaved by the cellular protease furin late in the exocytic pathway. During biosynthesis, the fusion protein and companion protein associate within the endoplasmic reticulum (ER) to form non-covalent heterodimers, a process required for proper folding and transport of the fusion protein. Viruses containing uncleaved p62 or prM have greatly reduced infectivity and fusion due to the interaction of the uncleaved companion subunit with the fusion protein to prevent HT formation (Heinz et al., 1994; Salminen et al., 1992). In the mature alphavirus, the E2 protein maintains a stable heterodimer interaction with E1 and forms most of the projecting "spiky" domain of the alphavirus envelope (Zhang et al., 2002a). In contrast, the mature flavivirus particle is almost smooth as most of the ectodomain of the prM protein is removed by furin (Zhang et al., 2003c). Following prM processing, the flavivirus E protein forms an E-E homodimer. Budding of the alphaviruses occurs at the plasma membrane and is dependent on the interaction of the E2 cytoplasmic tail with the viral nucleocapsid. Flaviviruses bud into the ER and budding can produce either complete virions or smaller subviral (nucleocapsid-deficient) particles (reviewed in Garoff et al., 1998; Garoff et al., 2004; Strauss et al., 1995).

The virus entry pathway has been most fully characterized for the alphaviruses but appears very similar for the flaviviruses (reviewed in Heinz and Allison, 2001; Kielian, 1995; Kielian et al., 2000). Virus binds to receptors on the plasma membrane via the alphavirus E2 protein or the domain III region of the flavivirus E protein. The virus is internalized by the constitutive process of endocytosis. Virus-membrane fusion is triggered by the mildly acidic pH of the endosome compartment, with a threshold pH of ~6.2 for wt SFV. This low pH causes the dissociation of the alphavirus E2/E1 heterodimer or the flavivirus E/E homodimer. The monomeric E1 or E protein then inserts into the target membrane and refolds to form the homotrimer. Homotrimer formation, fusion, and infection are specifically blocked by various inhibitors of endosome acidification, which act by raising the pH above the critical fusion threshold (Glomb-Reinmund and Kielian, 1998; Kielian, 1995). Infection is also specifically blocked by expression of dominant-negative versions of cellular proteins involved in the endocytic entry pathway (e.g., Sieczkarski and Whittaker, 2002; Sieczkarski and Whittaker, 2003).

The fusion of SFV, Sindbis, and TBE with liposomes is efficiently triggered by low pH treatment in vitro, and is strongly promoted by the presence of cholesterol in the target membrane (Corver et al., 2000; Kielian and Helenius, 1984; Smit et al., 1999; Stiasny et al., 2003). This sterol requirement is also observed in vivo using cholesterol-depleted insect cells, and involves the sterol 3β-hydroxy 1 group rather than the bulk physical effects of cholesterol (Lu et al., 1999; Phalen and Kielian, 1991; Vashishtha et al., 1998). The soluble fusion protein ectodomains of SFV, dengue, and TBE form homotrimers that are biochemically comparable to those formed by the full-length molecules (Gibbons and Kielian, 2002; Klimjack et al., 1994; Stiasny et al., 2002), which made possible the structural studies discussed above. The membrane insertion and trimerization of the ectodomains requires the presence of cholesterol in the target membrane (Klimjack et al., 1994), and is highly cooperative, producing rings of 5-6 homotrimers (Gibbons et al., 2003; Stiasny et al., 2004).

Other references relating to the present invention are Modis et al., 2003; Modis et al., 2004; Modis et al, 2005; Zhang et al., 2004; Vashishtha et al., 1998; Hung et al., 2004; Hilgard and Stockert, 2000; Jaiswal et al., 2004; Volk et al., 2004; Wu et al., 2003; Lakowicz, 1999; Owicki, 2000, and Ahn et al., 2002.

Summary. It is now clear that there is a second class of virus membrane fusion proteins exemplified by the alphaviruses and flaviviruses. Although markedly different in structure from the class I fusion proteins, the class II proteins also form a hairpin structure with the fusion peptide and transmembrane domains at the same end of a highly stable protein rod.

Due to the importance of viruses having class II fusion proteins, it would be desirable to further characterize the fusion process in these viruses and to identify ways to inhibit fusion. The present invention addresses that need.

SUMMARY OF THE INVENTION

The present invention is based in part on the inventors' discovery that addition of a soluble Domain III of a virus having a class II virus fusion protein to a eukaryotic cell inhibits infection of the cell by the virus and related viruses.

Accordingly, the present invention is directed to methods of inhibiting viral infection of a eukaryotic cell by a target virus having a class II virus fusion protein. The methods comprise combining the virus with an aqueous-soluble protein comprising a domain equivalent to a Domain III of an Alphavirus fusion protein, where the Domain III has SEQ ID NO:1.

In other embodiments, the invention is directed to methods of screening a test compound for the ability to inhibit infection by a virus having a class II viral fusion protein, the method comprising
 (a) combining the test compound with
  (i) an aqueous-soluble protein comprising a domain equivalent to a Domain III of an Alphavirus fusion protein, wherein the Domain III has SEQ ID NO:1, and
  (ii) a core homotrimer of the class II viral fusion protein, then
 (b) determining whether the aqueous-soluble protein and the core trimer are bound together. In these methods, reduced binding of the protein with the core homotrimer in the presence of the test compound indicates that the test compound inhibits infection by the virus.

The present invention is also directed to other methods of screening a test compound for the ability to inhibit infection by a virus having a class II viral fusion protein. These methods comprise (a) combining the test compound with a class II viral fusion protein,
where the class II viral fusion protein comprises a Domain I, a Domain II, and a Domain III, and where the Domain III portion further comprises a fluorescent molecule that is quenched upon fold-back of the Domain III region during trimerization, and (b) determining whether the test compound reduces quenching of the fluorescent molecule upon conditions where quenching occurs in the absence of the test compound. In these methods, reduced quenching of the fluorescent molecule indicates that the test compound inhibits infection by the virus.

In further embodiments, the invention is directed to aqueous-soluble proteins comprising a portion of a class II viral fusion protein, wherein the portion of the class II viral fusion protein comprises a domain equivalent to a Domain III of an Alphavirus fusion protein, wherein the Domain III has SEQ ID NO:1, and a region equivalent to at least a portion of a stem region of an Alphavirus fusion protein, wherein the stem region has SEQ ID NO:2.

BRIEF DESCRIPTION OF THE DRAWINGS

FIG. 4 shows a schematic of target protein strategies to follow the interaction of fluorescent dIII (light grey ball) with core HT. Interaction of dIII is shown either (1) during trimerization or (2) post-trimerization.

DETAILED DESCRIPTION OF THE INVENTION

The present invention is based in part on the inventors' discovery that addition of a soluble Domain III of a virus having a class II virus fusion protein to a eukaryotic cell inhibits infection of the cell by the virus and related viruses. See Liao and Kielian, 2006 and Example below. Without being bound by any particular mechanism, it is believed that the soluble Domain III binds to the class II virus fusion protein preventing foldback of the fusion protein Domain III during trimerization. The inventors have used this discovery to develop novel methods for inhibiting viral infection and for determining whether a test compound has the ability to inhibit viral infection. Novel compositions useful for these methods are also provided.

Accordingly, the present invention is directed to methods of inhibiting viral infection of a eukaryotic cell by a target virus having a class II virus fusion protein. The methods comprise combining the virus with an aqueous-soluble protein comprising a domain equivalent to a Domain III of an Alphavirus fusion protein, where the Domain III has SEQ ID NO:1.

Figure 1:
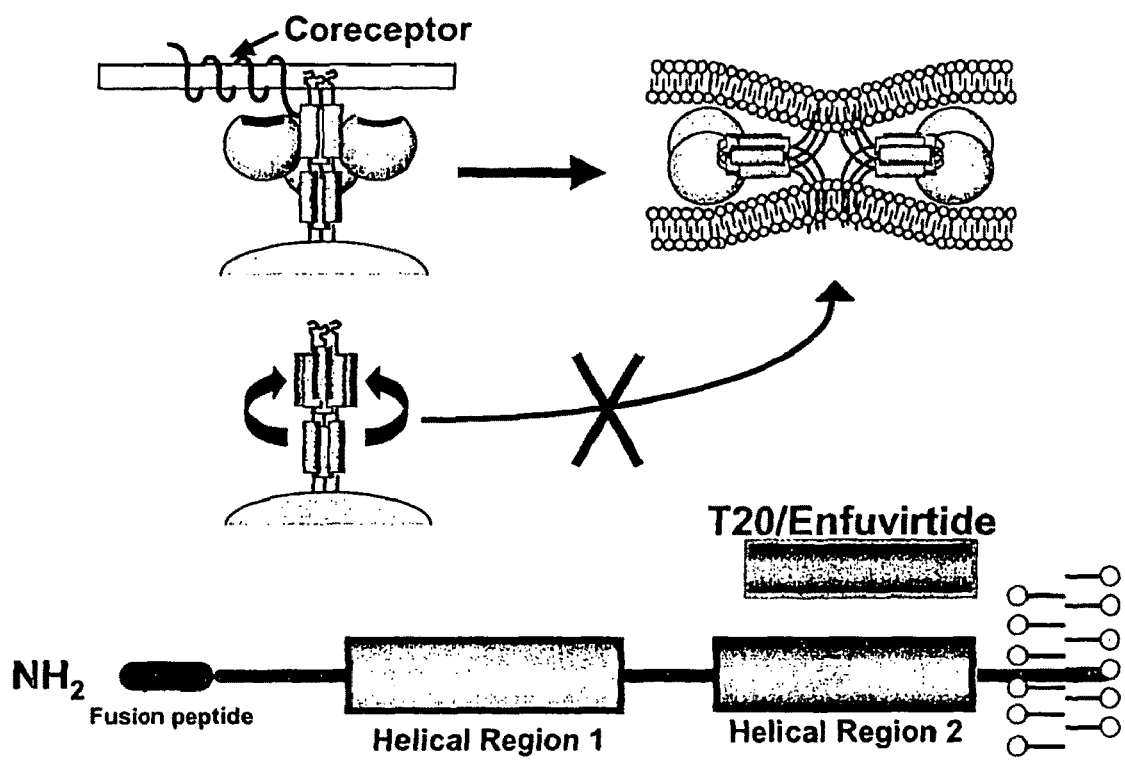
FIG. 1 is a diagram of the inhibition of HIV fusion by T20 peptide. T20 acts to inhibit the critical refolding reaction that drives HIV-1 membrane fusion (schematic courtesy of Dr. R. Doms).
Figure 2:
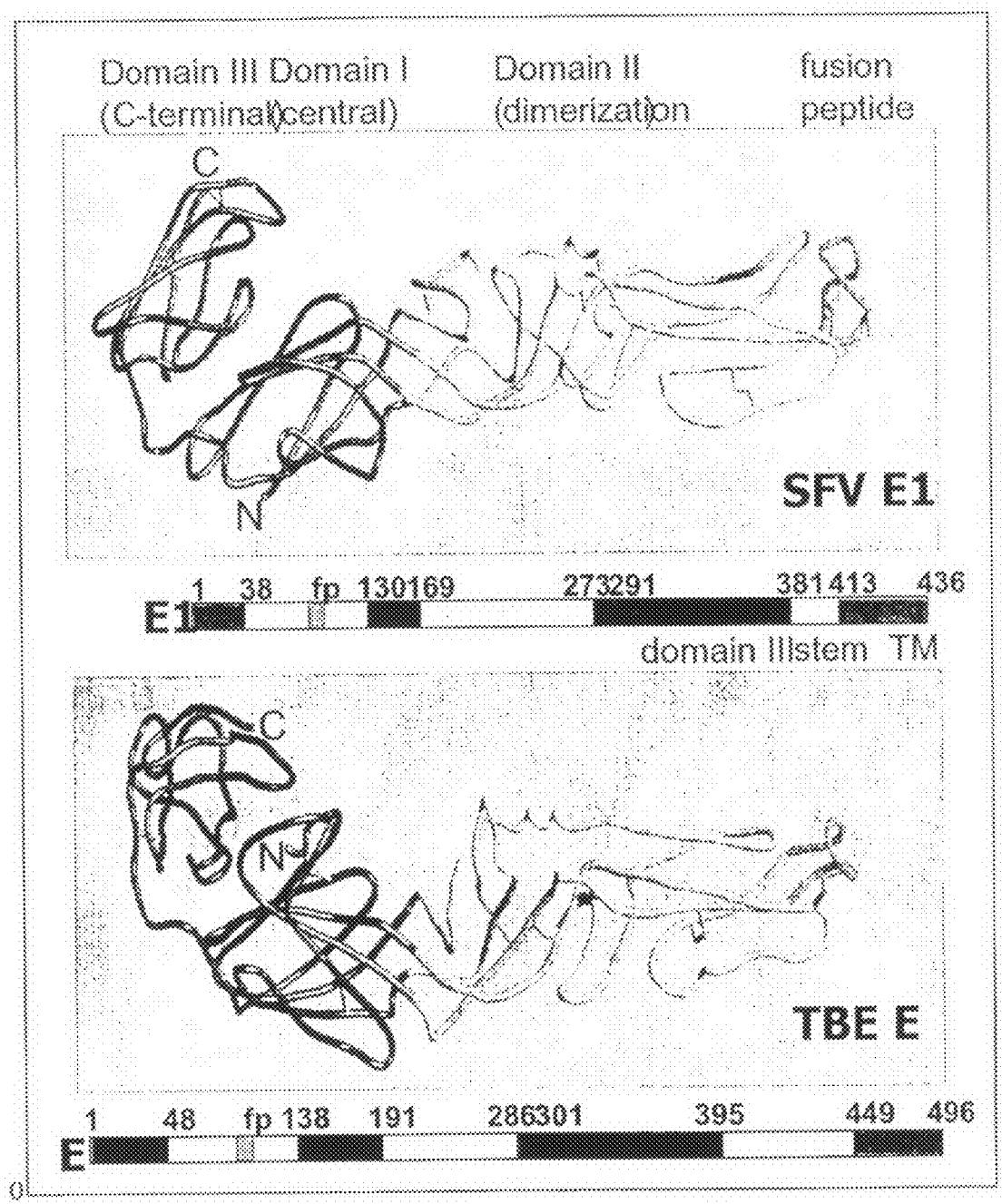
FIG. 2 is a ribbon model of the structure of the SFV E1 and TBE E proteins, from Lescar et al., 2001.

As used herein, a "domain" is a discrete portion of a protein having its own function and characteristic three-dimensional structure. A Domain III ("dIII", "domain III") is a recognized domain of a class II fusion protein with a structure and function equivalent to the domain III region of the Semliki Forest virus (SFV) class II fusion protein (E), where the domain III has the sequence of SEQ ID NO:1. A Domain III interacts with the central core of the trimer upon trimerization when part of a functional class II fusion protein. It comprises a portion of near the C-terminal domain of the SFV fusion protein. A Domain III is generally expected to have a ribbon structure substantially as depicted in FIG. 2, as shown for SFV and tick-borne encephalitis virus (TBE). The amino acid sequence need not have any homology with SEQ ID NO:1, but must only be part of a naturally-occurring class II fusion protein, or a derivative thereof, where the domain III interacts with the central core of the trimer upon trimerization. Thus, mutants of a naturally occurring domain III are envisioned as within the scope of a domain III, provided the mutant domain, if part of a class II fusion protein, is still capable of interacting with the central core of the trimer upon trimerization These methods are useful for inhibiting infection of any eukaryotic cell susceptible to a virus having a class II fusion protein, including plant cells and mammalian cells, e.g., human cells. Preferably, the cell is part of a living multicellular eukaryote, more preferably a mammal, and most preferably a human.

As used herein, "aqueous-soluble" means soluble in an aqueous solution and/or suspension, e.g. water, saline, buffered saline, and/or a physiological fluid such as blood, bile, or lymph.

The aqueous-soluble protein in these embodiments can comprise peptidomimetics as substitutes for one or more than one amino acid moiety. As used herein, an amino acid mimetic or peptidomimetic is a compound that is capable of mimicking a natural parent amino acid in a protein, in that the substitution of an amino acid with the peptidomimetic does not affect the activity of the protein. Proteins comprising peptidomimetics are generally poor substrates of proteases and are likely to be active in vivo for a longer period of time as compared to the natural proteins. In addition, they could be less antigenic and show an overall higher bioavailability. The skilled artisan would understand that design and synthesis of aqueous-soluble proteins comprising peptidomimetics would not require undue experimentation. See, e.g., Ripka et al., 1998; Kieber-Emmons et al., 1997; Sanderson, 1999.

In some preferred embodiments, the aqueous-soluble protein further comprises a region equivalent to at least a portion of a stem region of an Alphavirus fusion protein, wherein the stem region has SEQ ID NO:2. As shown in the Example, retaining on the aqueous-soluble protein at least a portion of the stem region of a class II fusion protein can improve the ability of the aqueous-soluble protein to inhibit infection. As used herein, the stem region of a class II fusion protein is the region equivalent to the stem region of SFV, having the sequence of SEQ ID NO:2. The stem region of SFV is 29 amino acids immediately toward the carboxy end of the fusion protein from the Domain III. In these embodiments, an equivalent stem region need not have homology to SEQ ID NO:2, but will be structurally similar. The skilled artisan could identify a stem region of any class II fusion protein without undue experimentation.

The aqueous-soluble protein preferably also further comprises a region equivalent to a DI/DIII linker region from an Alphavirus class II fusion protein, where the Alphavirus linker region has SEQ ID NO:11. The linker region defined herein as SEQ ID NO:11 is somewhat smaller than the linker region as identified in Roussel et al., 2006. The inclusion of this linker region also improves binding of the aqueous-soluble protein to the homotrimer. The skilled artisan could identify a linker region of any class II fusion protein without undue experimentation.

In additional embodiments, the aqueous-soluble protein further comprises an oligohistidine moiety (e.g., a His6). Such moieties are known to aid in purification of proteins that are engineered to have them, by virtue of their ability to bind to certain chromatography media. An example of an engineered His6 moiety is the first thirty-six residues of SEQ ID NO:7.

In some preferred embodiments of these methods, the aqueous-soluble protein comprises SEQ ID NO:1. The aqueous-soluble protein can be present in any concentration that effects inhibition of virus infection. As shown in the Example, that concentration can be as low as 50 nM, 100 nM, 250 nM, 500 nM, 1000 nM, 5000 mM, or greater.

The above-described aqueous-soluble proteins can be formulated without undue experimentation into a pharmaceutical composition for administration to a mammal, including humans, as appropriate for the particular application. Additionally, proper dosages of the compositions can be determined without undue experimentation using standard dose-response protocols.

Accordingly, the compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The compositions of the present invention can easily be administered parenterally such as for example, by intravenous, intramuscular, intrathecal or subcutaneous injection. Parenteral administration can be accomplished by incorporating the compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches (such as the well-known nicotine patch), ointments, creams, gels, salves and the like.

The present invention includes nasally administering to the mammal a therapeutically effective amount of the composition. As used herein, nasally administering or nasal administration includes administering the composition to the mucous membranes of the nasal passage or nasal cavity of the patient. As used herein, pharmaceutical compositions for nasal administration of a composition include therapeutically effective amounts of the composition prepared by well-known methods to be administered, for example, as a nasal spray, nasal drop, suspension, gel, ointment, cream or powder. Administration of the composition may also take place using a nasal tampon or nasal sponge.

These methods are expected to be useful for inhibiting infection for any virus having a class II fusion protein, including any such virus now known or later discovered. Class II fusion proteins are now known in the Alphavirus (e.g., Semliki Forest virus) (family Togaviridae), Flavivirus (e.g., Dengue virus) (family Flaviviridae), Hepacivirus (e.g., hepatitis C virus) (family Flaviviridae), and Phlebovirus (e.g., Sandfly fever virus) (family Bunyaviridae) (Garry and Garry, 2004). All members of the Togaviridae, Flaviviridae, and Bunyaviridae would therefore be expected to have type II fusion proteins. Additionally, while Togaviridae and Flaviviridae are positive strand RNA viruses, Bunyaviridae are negative strand RNA viruses. Further, Rhabdoviridae may also have type II fusion proteins. This indicates that viruses having class II fusion proteins are widespread.

Thus, in some embodiments of these methods, the target virus is an Alphavirus, for example Semliki Forest virus, eastern equine encephalitis virus, western equine encephalitis virus, or Venezuelan equine encephalitis virus. In other embodiments, the target virus is a member of the Flaviviridae, such as dengue virus, hepatitis C virus, Japanese encephalitis virus, tick-borne encephalitis virus, yellow fever virus, West Nile virus, bovine viral diarrhea virus, or swine fever virus. Additionally, the target virus can be a member of the Bunyaviridae, for example Crimean-Congo hemorrhagic fever virus or tomato spotted wilt virus. In some preferred embodiments, the target virus is Semliki Forest virus or dengue virus.

In preferred embodiments, the aqueous-soluble protein is a portion of the class II virus fusion protein of a virus in the same viral genus as the target virus. In more preferred embodiments, the aqueous-soluble protein is a portion of the class II virus fusion protein of the target virus.

These methods can be utilized in vitro (e.g., in cells in culture), or preferably, where the target virus is in a living eukaryote. In some preferred embodiments, the living eukaryote is a mammal.

The discovery of the effect the interaction of Domain III with the rest of the class III fusion protein, and the role of that interaction in viral infection, has led the inventors to develop assays for screening test compounds for the ability to inhibit viral infection.

Thus, the invention is also directed to methods of screening a test compound for the ability to inhibit infection by a virus having a class II viral fusion protein. The methods comprise
  (a) combining the test compound with
    (i) an aqueous-soluble protein comprising a domain equivalent to a Domain III of an Alphavirus fusion protein, where the Domain III has SEQ ID NO:1, and
    (ii) a core homotrimer of the class II viral fusion protein, then
  (b) determining whether the aqueous-soluble protein and the core trimer are bound together. In these embodiments, reduced binding of the protein with the core homotrimer in the presence of the test compound indicates that the test compound inhibits infection by the virus. Thus, these assays determine whether the test compound inhibits the interaction of the Domain III with the core homotrimer.

In some preferred embodiments, the aqueous-soluble protein further comprises a region equivalent to at least a portion of a stem region of an Alphavirus fusion protein. In these embodiments, the stem region of the Alphavirus fusion protein has SEQ ID NO:2. In other preferred embodiments, the aqueous-soluble protein further comprises a region equivalent to a DI/DIII linker region from an Alphavirus class II fusion protein. In these embodiments, the Alphavirus linker region has SEQ ID NO:11.

In some cases, the presence of an oligohistidine moiety also strengthens the interaction between the aqueous-soluble protein and the homotrimer. See Example. Thus, in some embodiments of these methods, the aqueous-soluble protein further comprises an oligohistidine moiety.

In other preferred embodiments of these methods, the aqueous-soluble protein comprises SEQ ID NO:1.

In preferred embodiments, the aqueous-soluble protein is labeled with a detectable label, generally to provide a detectable means to determine whether the aqueous-soluble protein and the core trimer are bound together. In these embodiments, the detectable label is a fluorescent molecule, a radioactive atom, an enzyme, or an antigen not naturally occurring in the aqueous-soluble protein. Preferably, the detectable label is a fluorescent molecule, where the determination step can utilize a method such as fluorescence polarization to determine binding. Such fluorescence polarization methods are known in the art. With fluorescent labels, the determination step can alternatively utilize fluorescence resonance energy transfer. FIG. 4 shows two strategies to follow the interaction of fluorescent Domain III with the core homotrimer.

In these embodiments, the core homotrimer need not be a complete or a wild-type form. It can include any mutations that do not substantially affect the ability of the Domain III to interact with it. It can also include peptidomimetics, as described above. Additionally, the core homotrimer can comprise a deletion or deletions from the wild-type form, provided that the mutant homotrimer is still capable of interacting with the Domain III. The core homotrimer can also be within an intact wild type or mutant virus. In some preferred embodiments, the core homotrimer does not comprise a domain equivalent to a Domain III of an Alphavirus fusion protein.

The present methods can be adapted to high throughput formats as are known in the art, e.g., using robotics. Additionally or alternatively, the methods can utilize immobilization of either the core homotrimer or the aqueous-soluble protein on a solid matrix, for example on a membrane, a bead or in a well such as a polystyrene plate. Such methods could be developed without undue experimentation.

Test compounds can also be screened for the ability to inhibit infection by a virus having a class II fusion protein by utilizing a core homotrimer with a Domain III portion that comprises a fluorescent molecule in such a position that the fluorescence of the fluorescent molecule is quenched upon fold-back of the Domain III upon trimerization of the fusion protein. A compound that prevents such quenching inhibits trimerization and infection. Alternatively, the fluorescence of the domain III portion may be protected from an added aqueous quencher upon trimerization. A compound that prevents such protection inhibits domain III foldback and infection.

Thus, in additional embodiments, the present invention is directed to methods of screening a test compound for the ability to inhibit infection by a virus having a class II viral fusion protein. The methods comprise
(a) combining the test compound with a class II viral fusion protein,
where the class II viral fusion protein comprises a Domain I, a Domain II, and a Domain III, and wherein the Domain III further comprises a fluorescent molecule that is quenched upon fold-back of the Domain III, and
(b) determining whether the test compound reduces quenching of the fluorescent molecule upon conditions where quenching occurs in the absence of the test compound. In these embodiments, reduced quenching of the fluorescent molecule indicates that the test compound inhibits infection by the virus.

Examples of residues of class II fusion proteins that could be fluorescently labeled, where the fluorescence would be quenched upon trimerization, are residues equivalent to Asp311, Phe312, Thr 338, Gln340, or His 331 of a Semliki Forest Virus class II fusion protein or Gln316 or His317 of a Dengue virus 2 class II fusion protein. Other such residues can be determined without undue experimentation by identifying suitable residues at the Domain III-core trimer interface.

The present invention is also directed to aqueous-soluble proteins comprising a portion of a class II viral fusion protein, where the portion of the class II viral fusion protein comprises
(a) a domain equivalent to a Domain III of an Alphavirus fusion protein, wherein the Domain III has SEQ ID NO:1, and
(b) a region equivalent to at least a portion of a stem region of an Alphavirus fusion protein, wherein the stem region has SEQ ID NO:2. Based on experimental results provided in the Example, such novel proteins are useful in that they prevent infection of eukaryotic cells by viruses with class II fusion proteins, and can be utilized in the screening assays described above.

The aqueous-soluble protein of these embodiments also preferably comprises a region equivalent to a DI/DIII linker region from an Alphavirus class II fusion protein. Here, the Alphavirus linker region has SEQ ID NO:11

In some preferred embodiments, these aqueous-soluble proteins comprise SEQ ID NO:1 and SEQ ID NO:2. Alternatively, the aqueous-soluble protein can comprise mutations, deletions, peptidomimetics, etc.

The class II viral fusion protein of these embodiments can be derived from any virus having such a protein. In preferred embodiments, the class II viral fusion protein is from a member of the Togaviridae, Flaviviridae, or Bunyaviridae. In this regard, the class II viral fusion protein can be from, e.g., an Alphavirus or a Flaviviridae.

Furthermore, the aqueous-soluble protein of these embodiments can further comprise a detectable label and/or a binding moiety, for example a fluorescent molecule, a radioactive atom, an enzyme, an antigen not naturally occurring in the aqueous-soluble protein, or an oligohistidine moiety. In some preferred embodiments, the detectable label is a fluorescent molecule; in other preferred embodiments the aqueous-soluble protein comprises an oligohistidine moiety as discussed above.

Preferred embodiments of the invention are described in the following example. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims that follow the example.

Example

Figure 3:
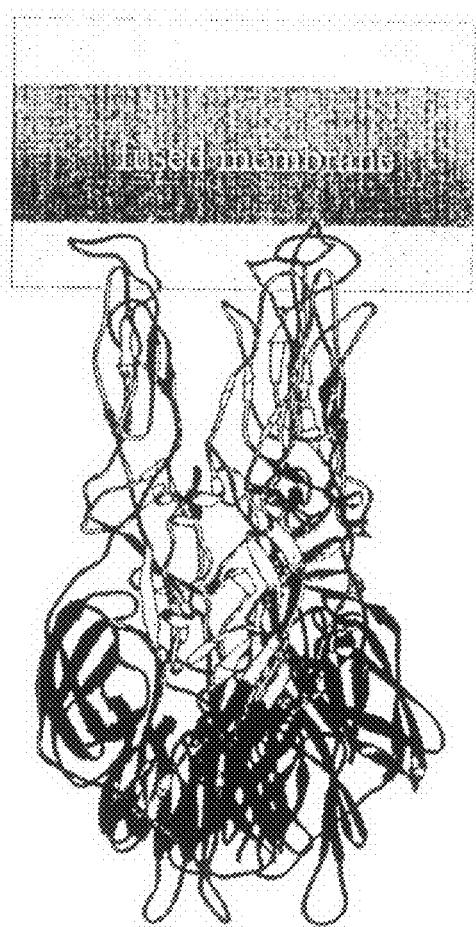
FIG. 3 is diagrams of SFV E1 HT. On the left, a ribbon model of a low pH-induced SFV E1* trimer structure showing model for membrane insertion (Gibbons et al., Nature 2004). On right is a schematic of the final. postfusion conformation of SFV E1 trimer showing fusion peptide (star), stem, and TM domains.
Figure 3:
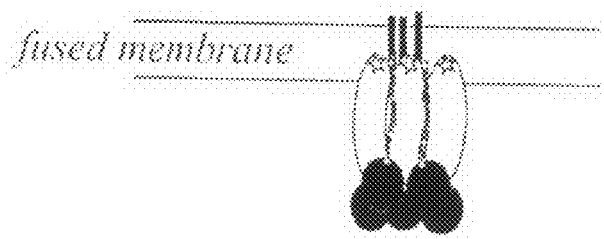
Figure 5:
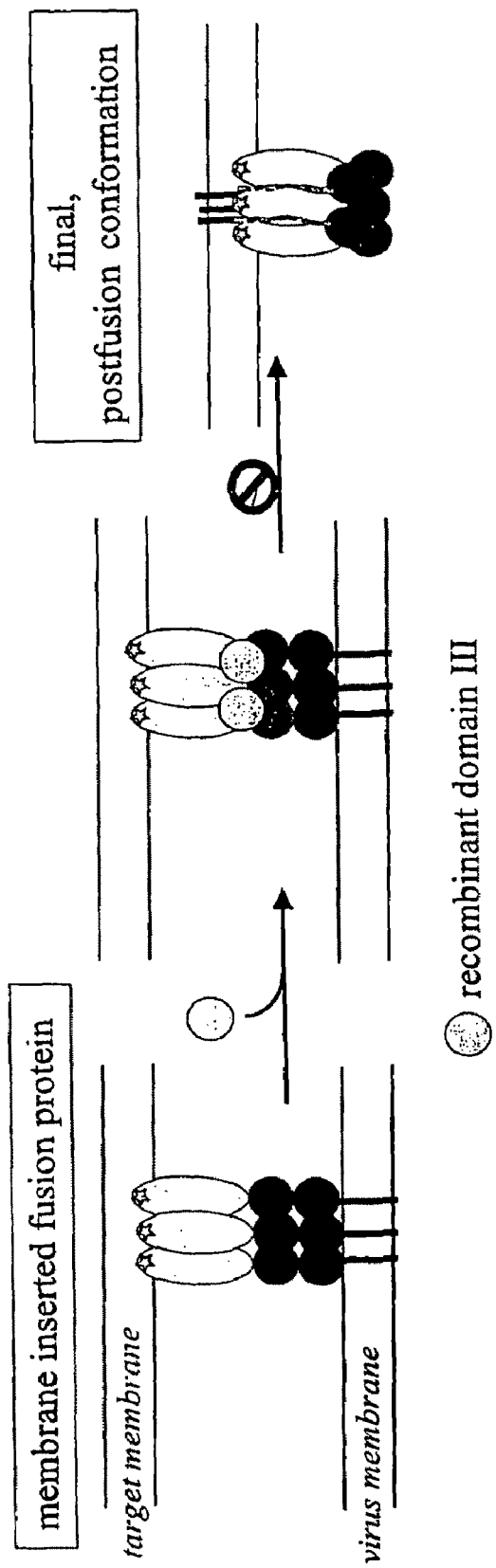
FIG. 5 is a schematic model for inhibition of SFV fusion by addition of soluble domain III.

Domain III from Class III Fusion Proteins Functions as a Dominant-Negative Inhibitor of Virus Membrane Fusion Rationale and domain III expression. The structure of the class II homotrimer suggests several features that might be targets for inhibition of the fusion reaction. The pH 7 form of the dengue virus E protein crystallized with a molecule of detergent bound in a hydrophobic pocket near the "hinge" region between domains 1 and II (Modis et al., 2003). As the hinge changes its angle during the transition to the trimer form, inhibition of this flexibility may block fusion and infection. Thus, molecules that dock into the hydrophobic pocket are potential antivirals (Modis et al., 2003). The structure of the fusion protein homotrimer reveals that the "stem" region of the protein interacts (or would be predicted to interact in the case of the dengue HT and TBE HT, which do not contain the stem) with an HT core region composed of domains I and II (see stem in FIG. 3 schematic). Therefore, the stem peptide and its HT interaction site are potential targets, analogous to the T20 peptide of HIV and its interaction site on the central coiled-coil (Bressanelli et al., 2004; Modis et al., 2004; Roussel et al., 2006; Kielian, 2006; Kielian and Rey, 2006). We have tested several stem peptides and antibodies to the stem region for their ability to inhibit Semliki Forest virus (SFV) HT formation and fusion. None of these reagents showed any inhibitory activity. Given that identification of peptide inhibitors of class I fusion reactions frequently requires screening of many candidate peptides, it is certainly possible that class II stem peptides will eventually work as antiviral reagents. However, we felt that it was important to consider the inhibitor question more broadly. The structure of the low pH-induced trimer revealed a striking movement of domain III towards the trimer tip, resulting in the interaction of domain III with the HT core (composed of domains I and II in trimeric form). This reorientation of domain III appears to be a critical feature of the formation of the class II hairpin. We therefore decided to test soluble forms of domain III as potential inhibitors (FIG. 5).

Several previous studies had demonstrated that flavivirus domain III could be produced in bacteria as fusion proteins (Volk et al., 2004), epitope-tagged proteins (Hung et al., 2004; Wu et al., 2003), or by refolding of the expressed molecule (Jaiswal et al., 2004). The structures of recombinant domain III from West Nile virus (Volk et al., 2004) and Japanese encephalitis virus (Wu et al., 2003) were determined by NMR and shown to be essentially identical to the structure of dIII in TBE E protein purified from virus (Rey et al., 1995). We took this information into account in our expression of the analogous alphavirus protein. SFV domain III is contiguous in the linear sequence of E1, and forms an Ig-like β-barrel structure with three disulfide bonds (FIG. 2).

Figure 6A:
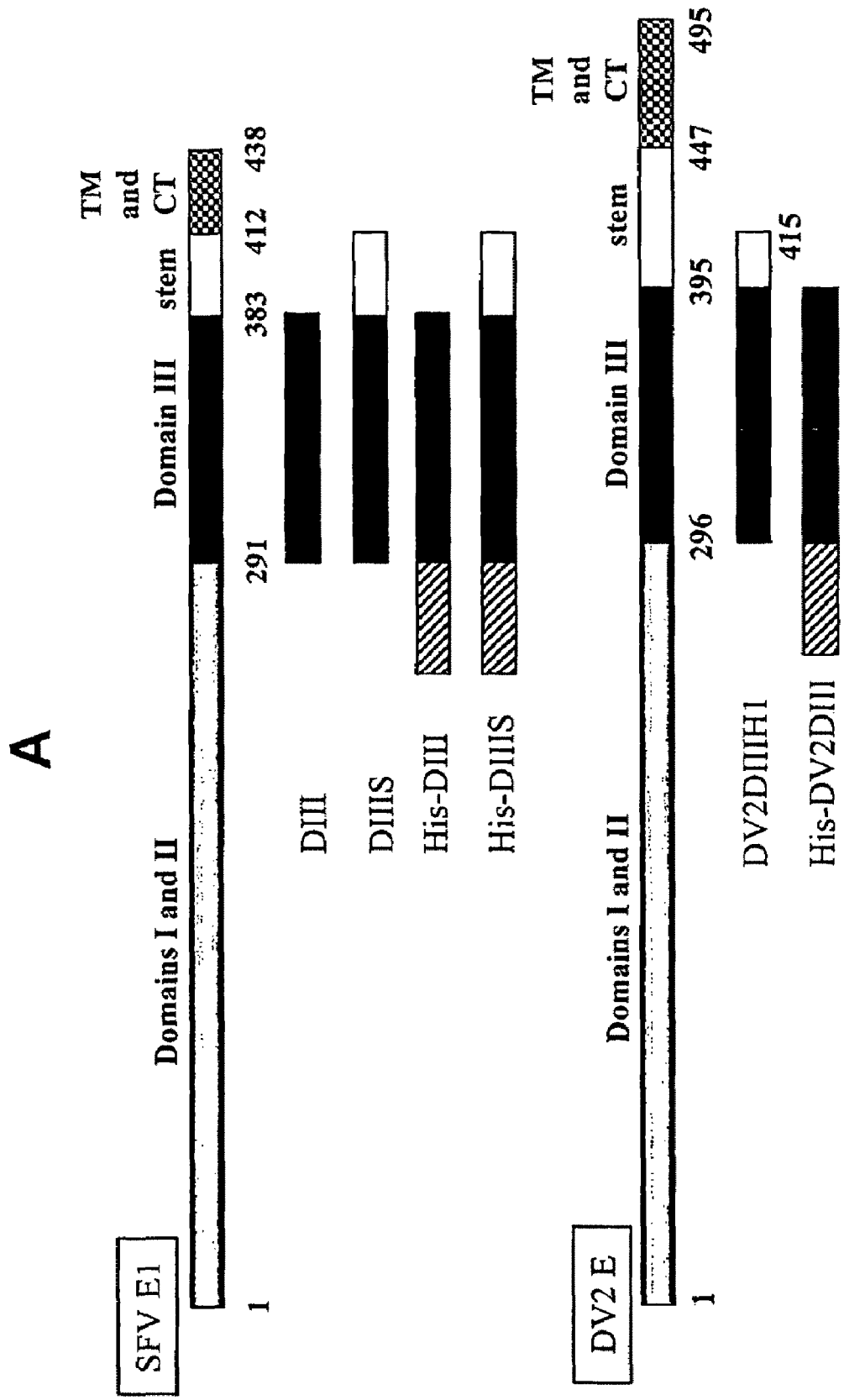
FIG. 6 is diagrams, photographs of autoradiographs, and a chart summarizing domain III proteins discussed in the Example. Panel A shows linear diagrams of primary sequences of SFV E1, DV2 E and domain III constructs, showing the boundaries of the domains, stem region, and transmembrane anchor region (TM). The SFV E1 domain III proteins are: DIII (residues 291-383), DIIIS (291-412), His-DIII (His-tag plus 291-383) and His-DIIIS (His-tag plus 291-412); the DV2 E domain III proteins are: DV2DIIIH1 (296-415) and His-DV2DIII (His-tag plus 296-395). The His-tag adds 36 residues at the N-terminus while untagged proteins contain an added methionine at the N-terminus. Panel B shows experimental results where 2 µg of each purified domain III protein was treated with or without 10 mM DTT, then alkylated and subjected to electrophoresis on a 16.5% acrylamide gel using a Tris-tricine buffer system. Marker proteins are shown on the left with their molecular masses listed in kilodaltons. Panel C is a chart of experimental results where the molecular mass of each domain III protein was measured by mass spectrometry and compared with that calculated from the primary amino acid sequence. The mass for DV2DIIIH1 was calculated without the added N-terminal methionine since the measured mass indicated that this residue was not contained in the protein.
Figure 6B:
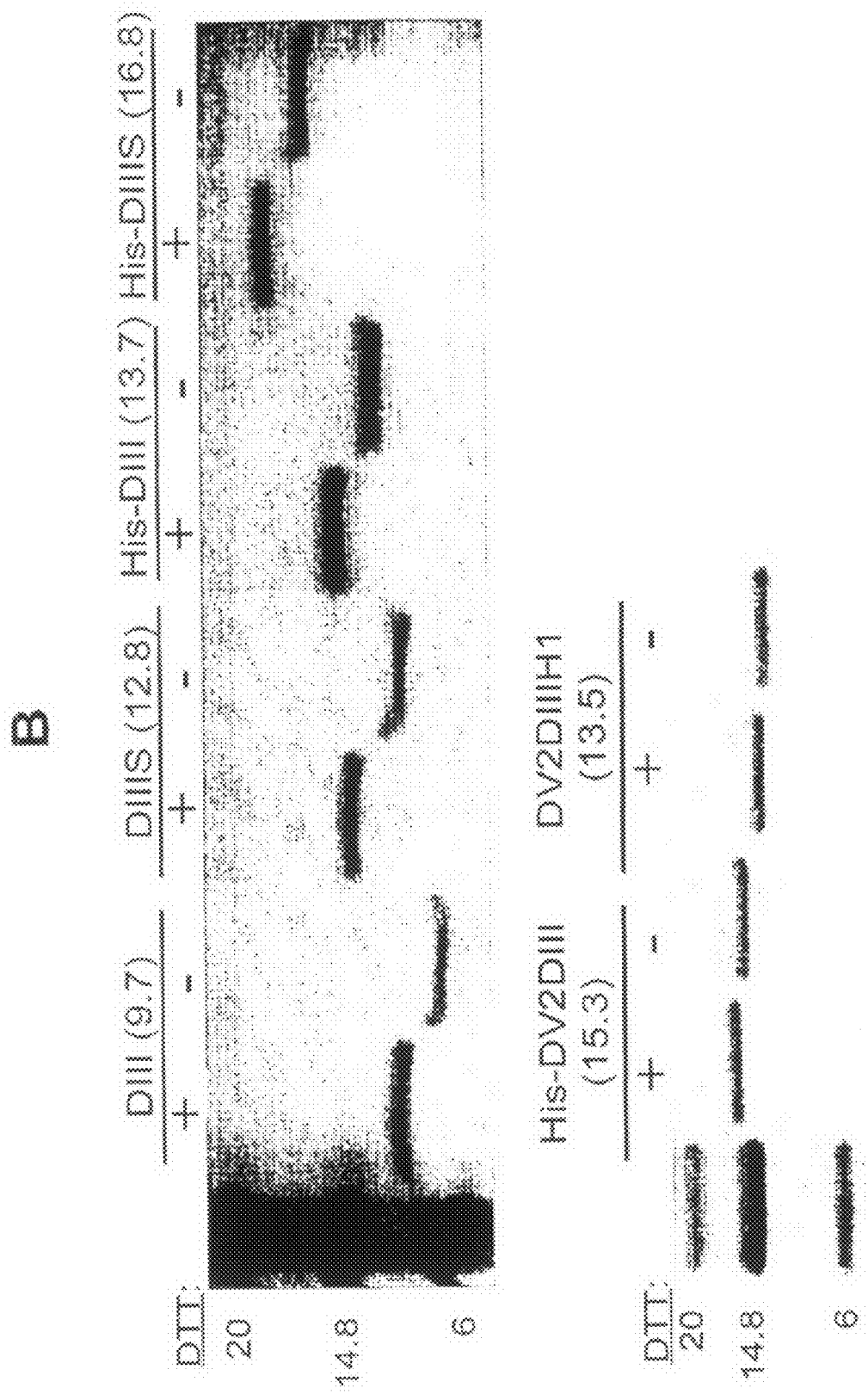

We prepared four domain III constructs for SFV, containing domain III with or without the stem region (DIIIS, DIII, respectively) and with or without an N-terminal His-tag (His-DIIIS, His-DIII) (FIG. 6A). We also prepared 2 constructs of domain III from the dengue 2 serotype: DV2DIIIH1 (DIII plus the helix 1 region of the stem) and His-DV2DIII (DIII with an N-terminal His tag). The proteins were expressed in E. coli, refolded using a fast dilution method successfully used to refold a number of proteins containing Ig-like domains (Zhang et al., 2002b), and purified by FPLC. All of the purified proteins migrate as a single band of the predicted size in SDS-PAGE and show a mobility shift upon reduction indicating the presence of disulfide bond(s) (FIG. 6B). FPLC analysis of the purified SFV proteins showed that they elute as single peaks at either neutral pH or pH 5.5 (data not shown). Analysis by mass spectroscopy confirmed the predicted protein sizes and suggested that the SFV domain III constructs contain three disulfide bonds since their determined masses are approximately 6 units less than those predicted if all 6 cysteines are reduced) (FIG. 6C). Similarly, the dengue domain III constructs appear to contain the single predicted disulfide. The disperse location of the cysteines in SFV domain III suggests that they cannot form aberrant disulfides without radically changing the protein fold (Lescar et al., 2001). Thus the presence of all three disulfide bonds, the proteins' high solubility (>10 mg/ml), and the biological activity described below strongly suggest that all of the SFV constructs have generated correctly folded domain III, similar to the preparations previously characterized for flavivirus domain III.

Inhibition of fusion and infection by SFV domain III preparations. We then screened the domain III preparations for inhibitory activity in virus fusion and infection assays. A simple, highly quantitative fusion assay extensively used by our lab is the fusion-infection assay (FIA) (Vashishtha et al., 1998; Zhang et al., 2003b). In this assay, serial dilutions of virus are added to cells on ice and allowed to bind in the cold. The unbound virus is washed away, and the cells with bound virus are treated briefly (1 min at 37° C.) at low pH to trigger the fusion of the virus with the plasma membrane of the cell. This fusion results in virus infection. The cells are then cultured overnight in the presence of 20 mM $NH_4Cl$ to prevent secondary infection, and the cells infected due to the low pH pulse are quantitated by immunofluorescence. Under these conditions, we could test the effects of domain III preparations during the binding step, the fusion step, and the post-fusion culture step.

Figure 7A:
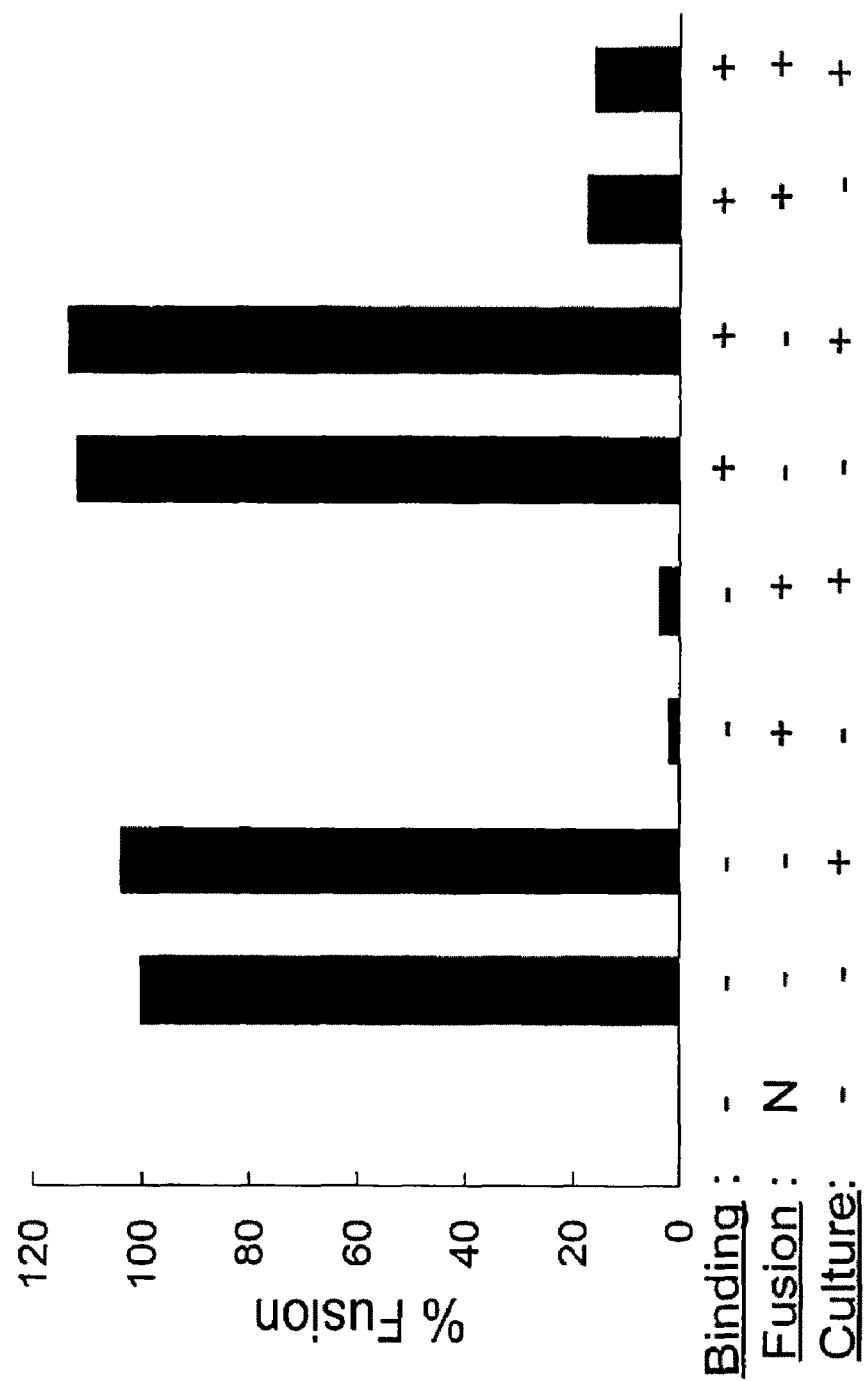
FIG. 7 is graphs of experimental results showing that SFV E1 domain III proteins inhibited SFV fusion with target cell membranes. In the experiment summarized in Panel A, SFV was added to BHK cells (MOI ~0.002) for 90 min on ice (binding). The cells were then incubated at pH 7.4 (indicated as "N") or at pH 5.5 at 37° C. for 1 min (fusion), and cultured at 28° C. overnight in medium containing 20 mM $NH_4Cl$ (culture). The presence or absence of 4 µM His-DIII in each step is indicated by +/−. Infected cells were quantitated by immunofluorescence. Results are shown as percent of control infection in the absence of any added His-DIII. Panel B shows the concentration dependence of domain III inhibition as determined using the assay in Panel 7A and adding the indicated concentrations of domain III proteins only during the 1 min low pH treatment. Data are a representative example from 2 independent experiments.
Figure 7B:
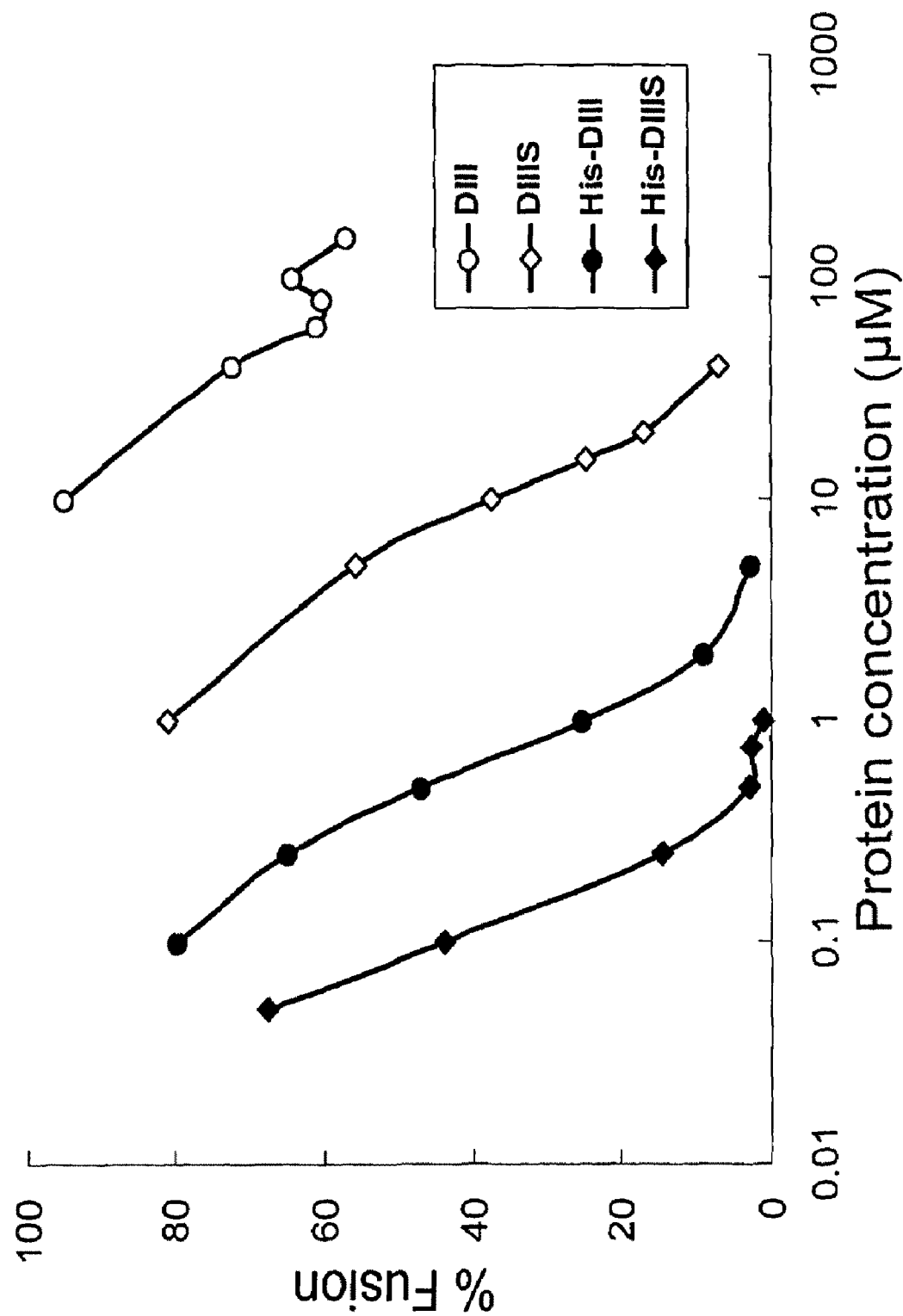

As shown in FIG. 7A, 4 μM His-DIII almost completely inhibited SFV infection of BHK cells, but only when present during the low pH-induced fusion step. Similar results were obtained for His-DIIIS (data not shown). In agreement with studies showing that alphavirus-receptor interaction is mediated by the E2 protein (Strauss and Strauss, 1994), His-DIII did not inhibit virus-cell binding as assayed by the FIA (FIG. 7A) or by quantitation of cell-associated radiolabeled SFV (data not shown, and FIG. 11C below). Pre-incubation of the virus with His-DIII at 37° C. at neutral pH had no effect on subsequent FIA (data not shown). Inhibition by domain III was comparable when virus was prebound to the cells at pH 6.5, 6.8, 7.4, or 8.0, or when the low pH pulse was at pH 5.5 or 6.0 (data not shown). Comparison of the 4 SFV domain III constructs showed that the strongest inhibition was obtained with His-DIIIS (IC50 ~0.1 μM), followed by His-DIII (IC50 ~0.5 μM), DIIIS (IC50 ~6 μM) and DIII which gave ~60% inhibition at a concentration of ~80 μM (FIG. 7B). Thus, the presence of both the stem region and the N-terminal His-tag resulted in increased effectiveness. While enhancement by the stem region is suggested from the structure of the low pH-induced homotrimer, the reason for the increase in inhibition observed with the His-tagged protein is not known, and presumably reflects a stabilization of the domain III-E1 interaction, as discussed below.

Figure 8A:
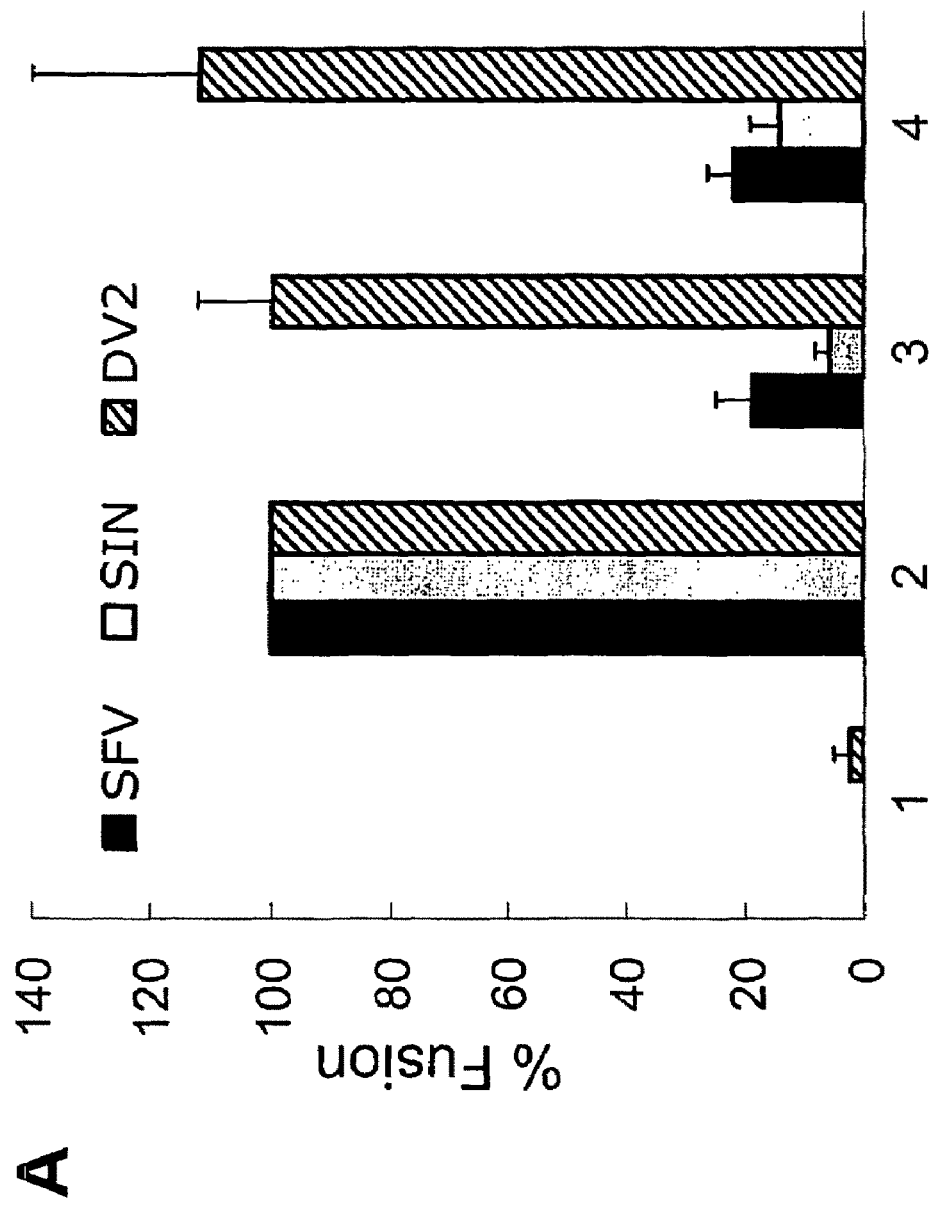
FIG. 8 is graphs of experimental results showing the inhibitory effect of domain III proteins on class II virus fusion, which shows broad spectrum and specificity inside the virus genus.

The specificity of inhibition was addressed by comparing the effect of SFV domain III on fusion of the alphavirus Sindbis (SIN) and the flavivirus dengue 2 (DV2). The sequence of domain III is ~50% identical between SFV and SIN, while the DV2 E protein shows no detectable sequence conservation with the alphavirus fusion proteins overall or in the domain III region. SFV, SIN, and DV2 all showed efficient fusion upon treatment at pH 5.5, and little fusion at pH 7.4 (FIG. 8A). Inclusion of SFV His-DIII or His-DIIIS during the low pH pulse inhibited SIN fusion with comparable (or even slightly higher) efficiency as SFV fusion. Neither SFV domain III preparation caused any inhibition of DV2 fusion.

Figure 8B:
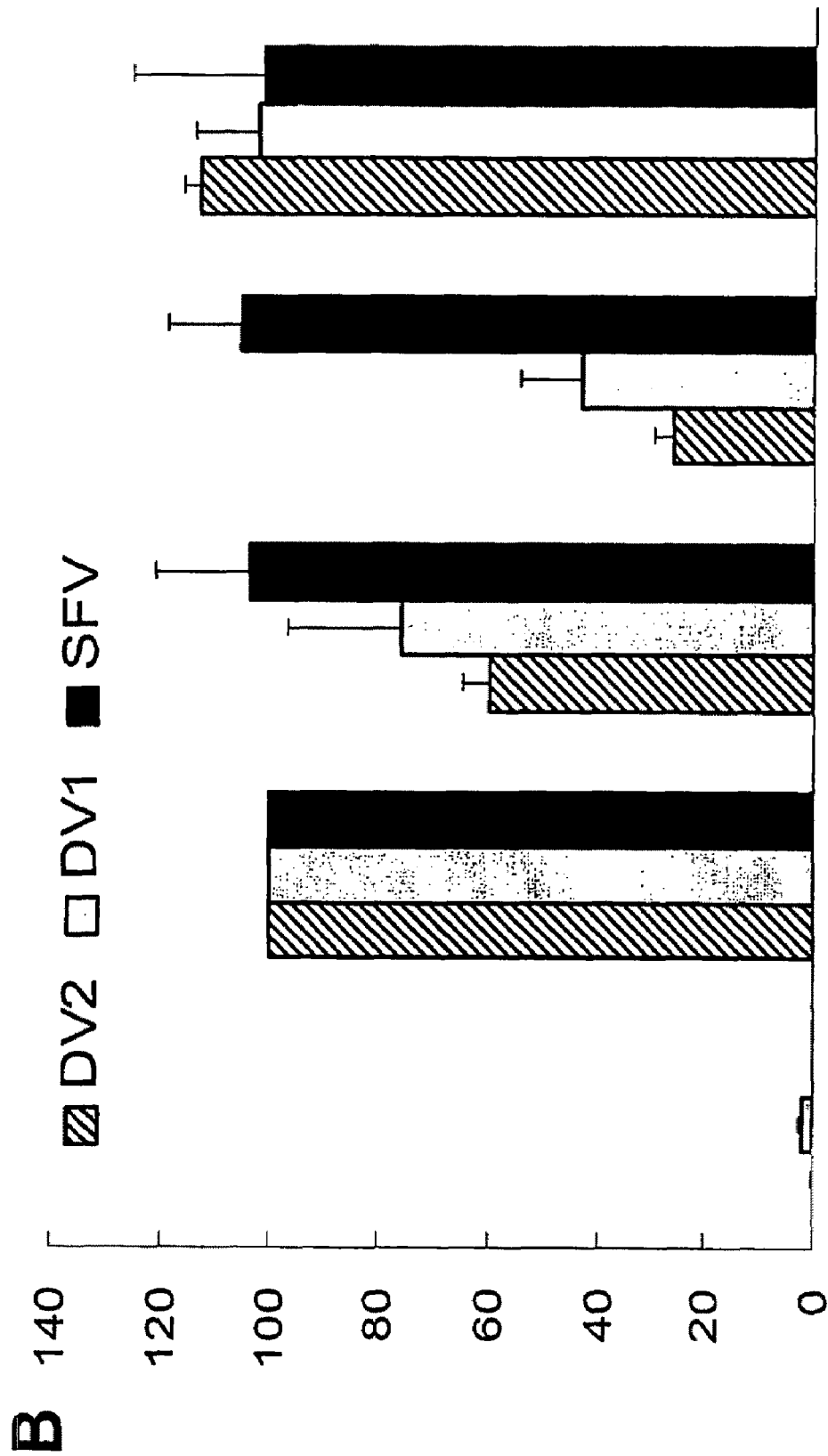

To address the general applicability of domain III inhibition to class II fusion, we used the His-DV2DIII and DV2DIIIH1 protein preparations and tested their ability to inhibit fusion by the DV2 and DV1 serotypes of dengue virus. These two serotypes show ~60% sequence identity in domain III. Unlike alphaviruses, flavivirus-receptor binding is directly mediated by the membrane fusion protein, and maps primarily to domain III. Prior studies of flavivirus domain III showed that it could block virus-cell binding when added prior to or concurrently with virus. We therefore prebound DV1 and DV2 to cells in the cold and added domain III only during the one minute pH pulse used to trigger fusion. As shown in FIG. 8B, the DV2DIIIH1 protein strongly inhibited both DV1 and DV2 fusion (~70% inhibition at a concentration of 50 µM), but showed no activity against SFV. Interestingly, His-DV2DIII did not inhibit fusion suggesting a possible role for the helix 1 stem region. Treatment at 37° C. for 1 min with either DV domain III preparation did not release bound virus from the cell membrane, implying that domain III inhibition was not due to effects on virus-receptor interaction (data not shown). Together these results strongly suggest that inhibition by DV2DIIIH1 occurred by effects on membrane fusion rather than by effects on virus binding. Thus, domain III can act as a specific inhibitor of the class II membrane fusion reaction. The observed cross-inhibition within the alphaviruses and flaviviruses suggests that key domain III amino acid contacts may be conserved within each virus genus.

Figure 9:
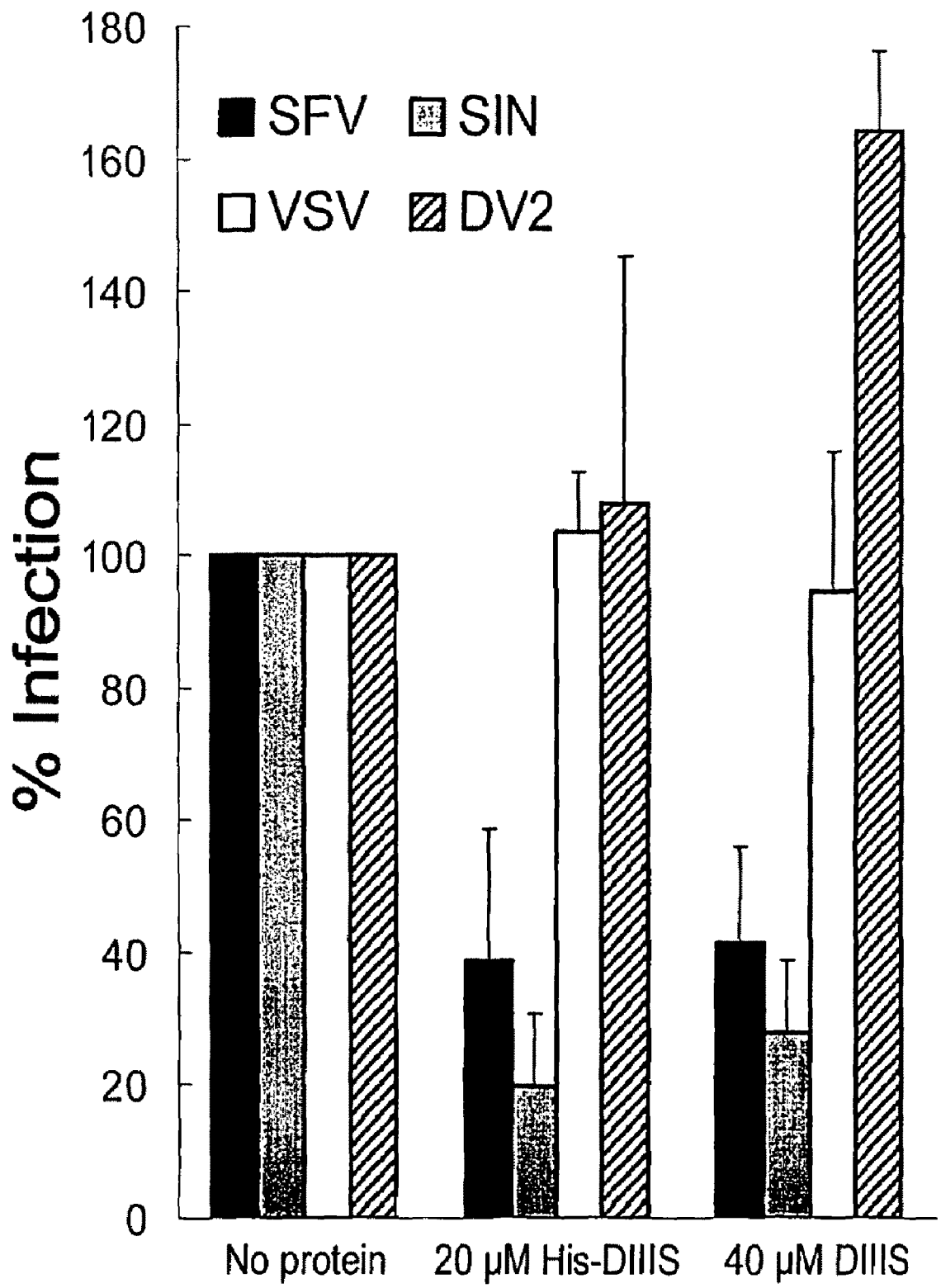
FIG. 9 is a graph of experimental results where SFV E1 domain III proteins inhibited SFV and SIN (Sindbis virus, an alphavirus) infection in the endocytic pathway. SFV, SIN, VSV and DV2 were diluted in medium of pH 7.2 containing the indicated concentrations of domain III. Viruses were incubated with BHK cells for 1 h at 20° C. to allow endocytic uptake. Infection was blocked by addition of medium containing 20 mM $NH_4Cl$, the cells were incubated overnight and infected cells quantitated by immunofluorescence. Data are shown as percent of control infection in the absence of domain III, and are the average of 3 independent experiments.

Since alphavirus-receptor binding is not mediated by the E1 protein, we used this system to test the ability of domain III proteins to inhibit virus fusion from within the endosome, the physiological route of virus infection. We infected BHK cells with SFV, SIN, vesicular stomatitis virus (VSV), or DV2 in the presence or absence of 20 µM His-DIIIS or 40 µM DIIIS. VSV, an unrelated rhabdovirus, and DV2 are important controls since these viruses also infect cells by endocytosis and low pH-triggered fusion (Matlin et al., 1982). After a 1 hour endocytic uptake period, 20 mM NH$_4$Cl was added to prevent further infection, and the primary infected cells were quantitated by overnight culture and immunofluorescence as described above. As shown in FIG. 9, infection by both alphaviruses was significantly inhibited by the inclusion of either the His-tagged or untagged forms of domain III plus stem. In contrast, VSV and DV2 infection were not inhibited, and DV2 infection was actually enhanced somewhat by DIIIS. Inhibition of alphavirus endocytic infection by His-DIIIS required a higher concentration than in the FIA, and also showed less efficacy versus untagged DIIIS than in the FIA. This could reflect relatively inefficient endocytic uptake of His-DIIIS by the cells or differential routing of virus and domain III within the endocytic pathway. While targeting of domain III to the endosomal site of virus fusion is probably not optimized, it is already clear that domain III can block fusion and infection under physiological virus entry conditions.

Figure 10A:
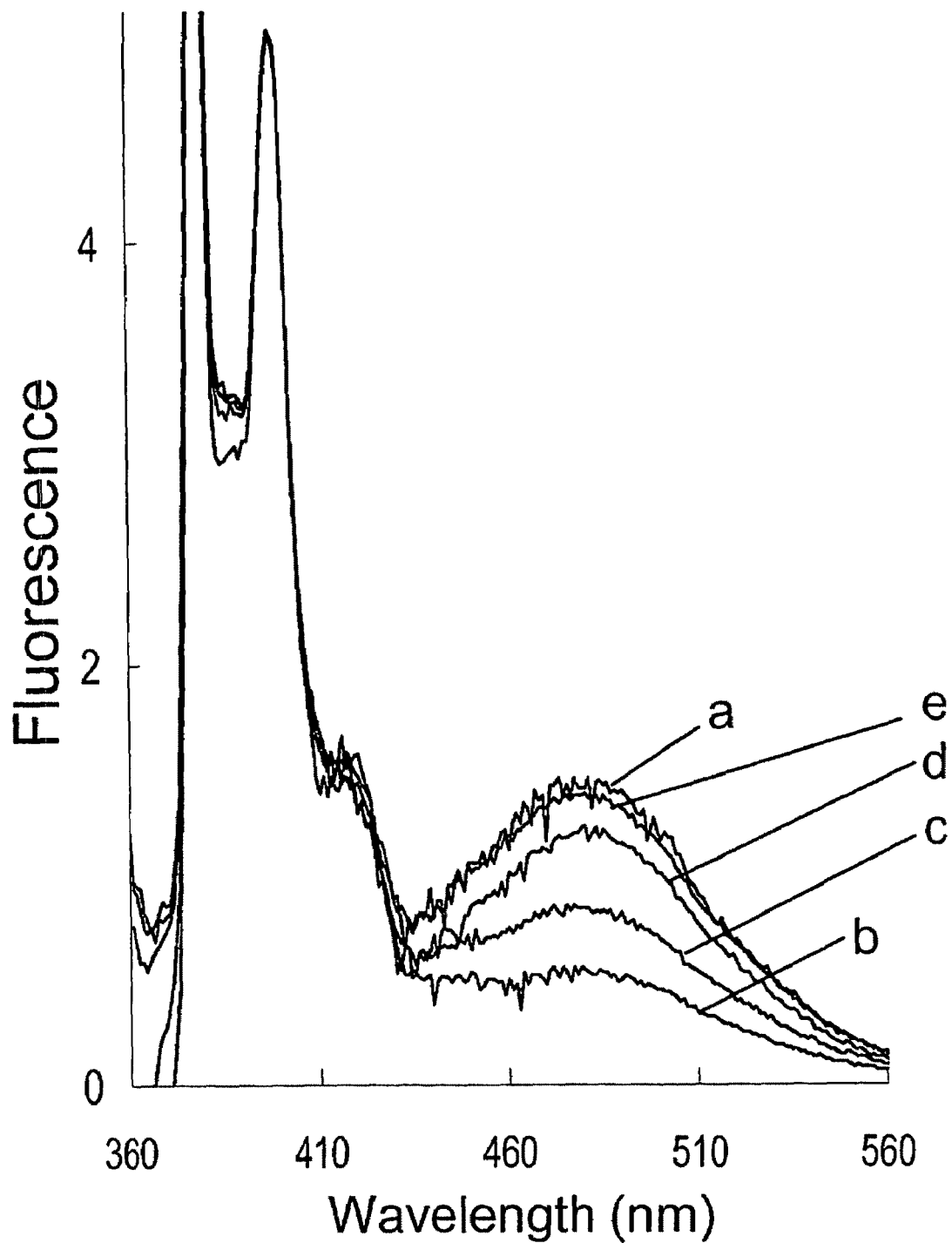
FIG. 10 is a fluorescence scan and a graph showing experimental results where SFV E1 domain III proteins inhibited the lipid mixing step of fusion. Panel A is a fluorescence scan of pyrene-labeled SFV fused with BHK cells. Pyrene-labeled SFV was pre-bound to BHK cells and incubated at 37° C. for 1 min in pH 7.4 medium without domain III protein (curve a), in pH 5.5 medium without domain III protein (curve b), or in pH 5.5 medium with 1 µM (curve c), 5 µM (curve d) or 8 µM (curve e) His-DIIIS. Background fluorescence from cells alone was subtracted and the fluorescence emission was normalized for each sample by setting the monomer peak at 397 nm to 5 (arbitrary units). Data shown are a representative example from 3 independent experiments. Panel B is a graph showing a comparison of inhibition of lipid mixing by domain III proteins. The fusion between pyrene-labeled SFV and BHK cells was assayed as in Panel 10A in the presence of the indicated concentrations of domain III proteins. The difference between the excimer/monomer (Ex/M) ratio at pH 7.4 and after treatment at pH 5.5 without domain III was defined as 100% (control). The difference between the pH 7.4 sample and each experimental sample was determined and expressed as a percent of this control difference. Data shown are the average from 3 independent experiments.
Figure 10B:
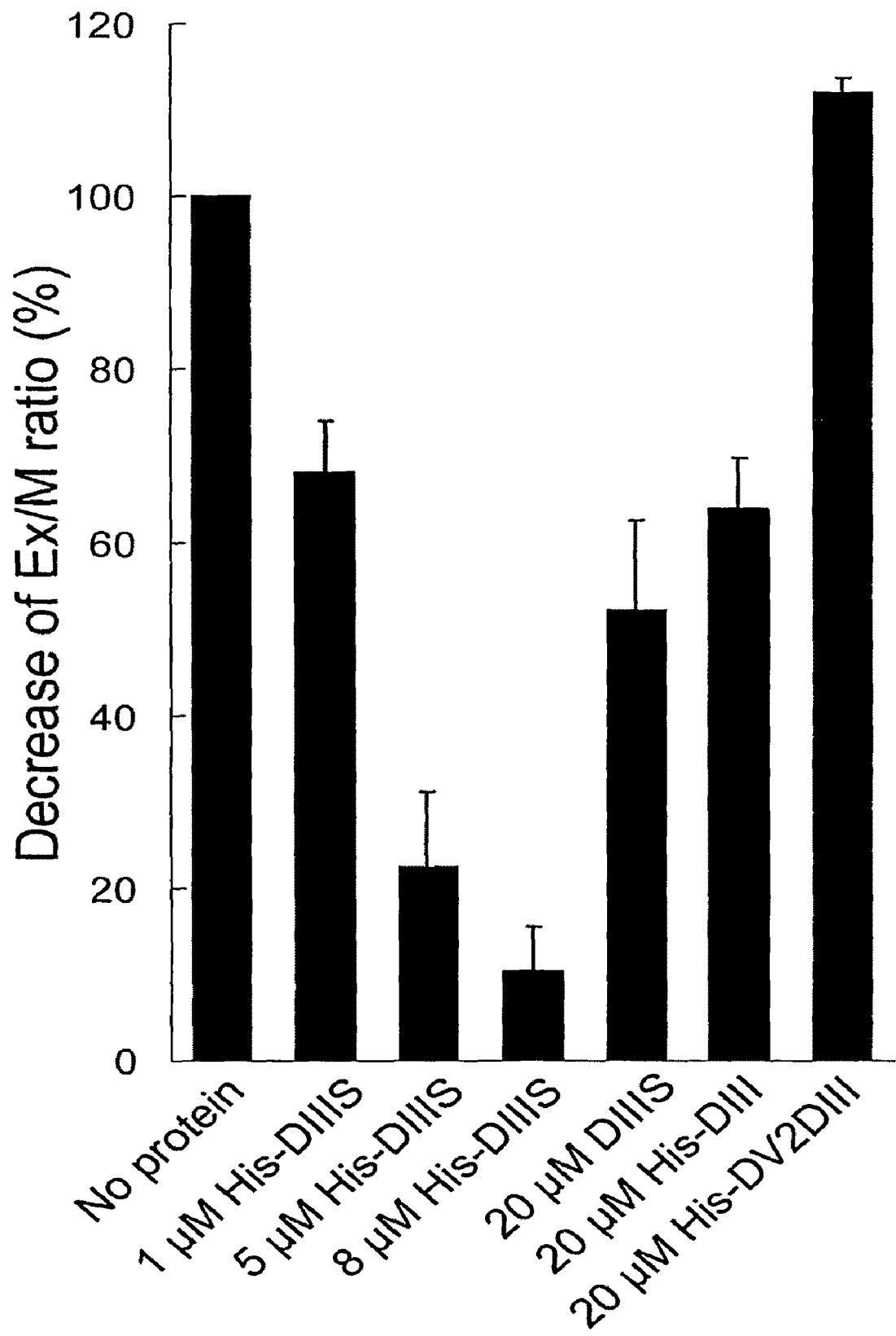

Exogenous domain III blocks the initial mixing of the virus and cell membranes. Class II virus fusion initiates through the interaction of the fusion loop with the target membrane, and progresses through an initial lipid mixing stage termed hemifusion, in which the outer leaflets of the virus and target membranes mix (Zaitseva et al., 2005). This stage is followed by the opening of a fusion pore, which then widens to give complete fusion and content mixing, the end stage of fusion monitored by the FIA. To test for the effects of domain III on initial lipid mixing and hemifusion, we followed the loss of the pyrene excimer peak upon fusion of pyrene-labeled SFV with unlabeled target cells (Chatterjee et al, 2002). Pyrene-labeled SFV was bound to cells in the cold and pulsed at low pH in the presence or absence of domain III. We then determined the fluorescence emission spectrum of each virus-cell mixture and compared the ratio of the excimer and monomer peaks (Chatterjee et al, 2002). Untreated virus (data not shown) or virus treated at pH 7.4 showed a strong excimer peak, with an excimer to monomer ratio of ~0.28 (FIG. 10A, curve a). Virus treated at pH 5.5 showed efficient fusion with the cell plasma membrane, as reflected in the decrease of the excimer peak and an excimer/monomer ratio of ~0.10 (curve b). The presence of His-DIIIS caused a concentration-dependent inhibition of the lipid mixing step (curves c-e). No effect was observed when His-DIIIS was added to the sample after low pH treatment (data not shown). As observed in the FIA, the His-DIIIS form of domain III showed the highest activity, with >90% inhibition of fusion at 8 µM (FIG. 10B). Both His-DIII and DIIIS showed significant inhibition at 20 µM, while the dengue virus protein showed no inhibition at 20 µM. A higher concentration of His-DIIIS was required to completely inhibit pyrene virus fusion compared to the FIA, reflecting either an intrinsic difference in the inhibitor sensitivity of lipid mixing vs. content mixing, or the higher concentration of virus used in the pyrene vs. FIA experiments.

Figure 11A:
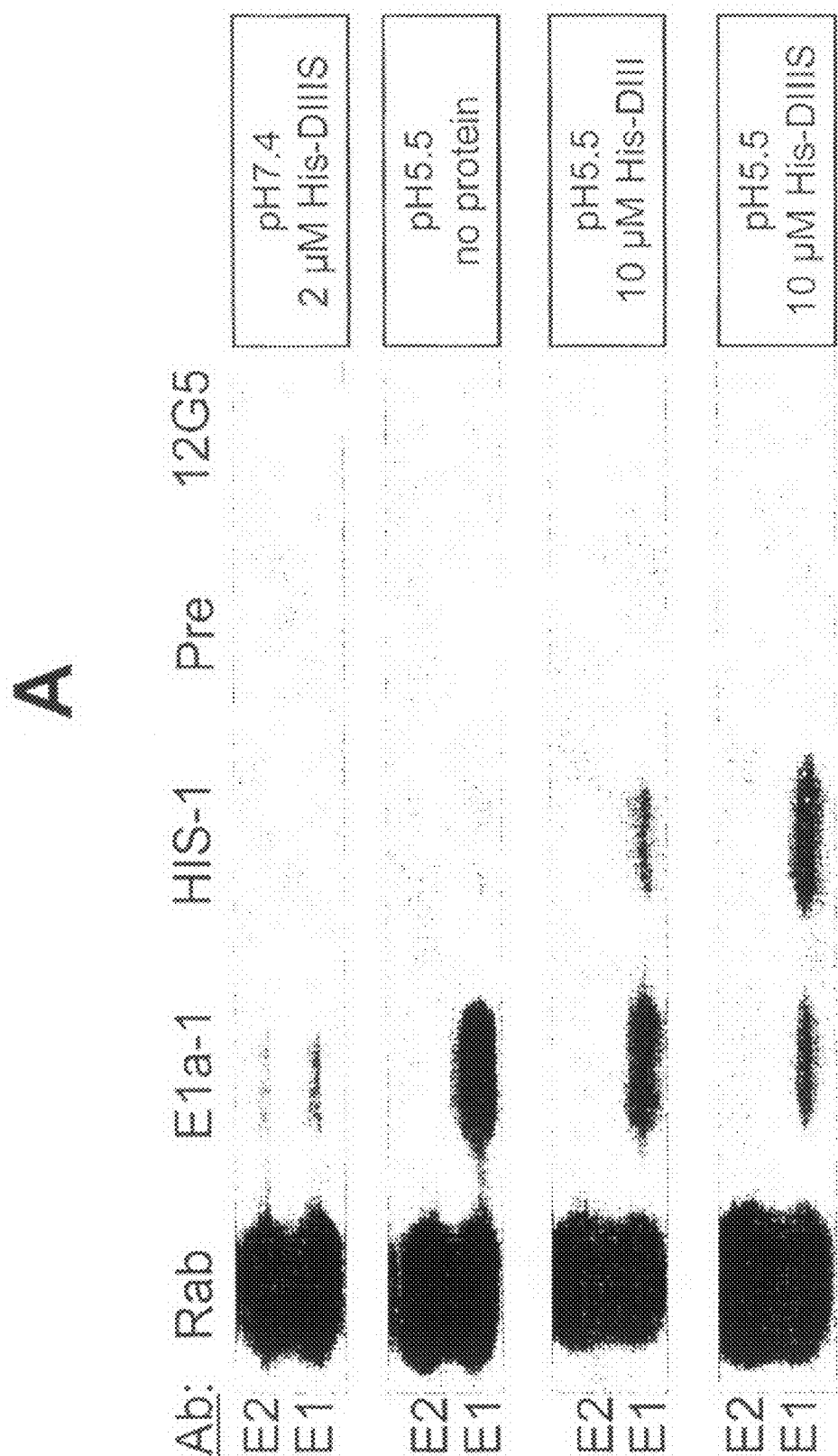
FIG. 11 is photographs of autoradiographs and a graph of experimental results showing that SFV domain III proteins bind to trimeric E1 during the fusion reaction. In the experiment summarized in Panel A, $^{35}S$-labeled SFV was bound to BHK cells on ice and treated at pH 7.4 or 5.5 at 37° C. for 1 min in the presence of the indicated domain III proteins. Cells were then lysed and immunoprecipitated with a rabbit polyclonal antibody against the SFV E1 and E2 protein (Rab), a mAb against the low pH conformation of E1 (E1a-1), a mAb against the His-tag (HIS-1), rabbit pre-immune serum (Pre), or an isotype-matched irrelevant mAb (12G5). Samples were analyzed by SDS-PAGE and fluorography. Panel B is a graph showing quantitation of samples prepared as in 11A using the indicated concentrations of His-DIII or His-DIIIS. "N" indicates 1 min treatment at pH 7.4 with 2 µM His-DIIIS. The total E1 in each sample was defined as the amount of E1 immunoprecipitated by RAb. Data are a representative example of 2 independent experiments. Panel C is autoradiographs showing that exogenous domain III proteins decreased the amount of SDS-resistant E1 homotrimer. Samples were prepared as with Panel 11B. An aliquot of the cell lysate was treated with SDS-sample buffer at 30° C. and analyzed by SDS-PAGE and fluorography. The position of the SDS-resistant homotrimer is indicated. Panel D is an autoradiograph showing that domain III selectively interacts with a trimeric form of E1. Fusion reactions were induced at pH 7.4 or pH 5.5 in the presence of 10 µM His-DIII as in Panel 11A. Samples were immunoprecipitated with the indicated antibodies and then digested with trypsin as indicated. The amount of trypsin-resistant E1 was quantitated and expressed as a percent of the non-trypsinized E1 for each sample. Data shown are a representative example of 2 independent experiments.

Interaction of domain III with E1 during fusion. If domain III is inhibiting virus fusion by preventing the fold-back of the full-length viral E1, it may interact stably with the E1 protein during inhibition. To assay for such interaction, we used radiolabeled SFV and His-DIII or His-DIIIS in the FIA. Following the low pH-treatment step, the cells were lysed in the non-ionic detergent octyl-glucoside, which we have shown fully solubilizes membrane-inserted E1, disrupts inter-trimer interactions, and maintains trimer structure (Gibbons, 2004a). Aliquots of the samples were immunoprecipitated using either a polyclonal antibody to quantitate the total E1 and E2 proteins, monoclonal antibody E1a-1, which specifically recognizes the acid-conformation of E1 (Ahn et al., 1999), an antibody that recognizes the His-epitope on domain III, or two control antibodies. SDS-PAGE demonstrated equivalent amounts of radiolabeled virus proteins present in cells treated at neutral or low pH with or without domain III, confirming that domain III does not release bound virus from the cell (FIG. 11A). Upon acid treatment the E1 subunit was efficiently recognized by the acid-specific monoclonal antibody. Inclusion of either His-DIII and His-DIIIS during low pH treatment resulted in co-immunoprecipitation of the E1 protein by the antibody to the His-tag. Similar to the inhibition of fusion activity, the interaction with E1 occurred only when domain III was present during the low pH treatment step, and not at neutral pH. The His-DIIIS protein preparation showed more efficient co-immunoprecipitation than His-DIII, in keeping with the more efficient inhibition of fusion by the stem-containing form of E1.

Figure 11B:
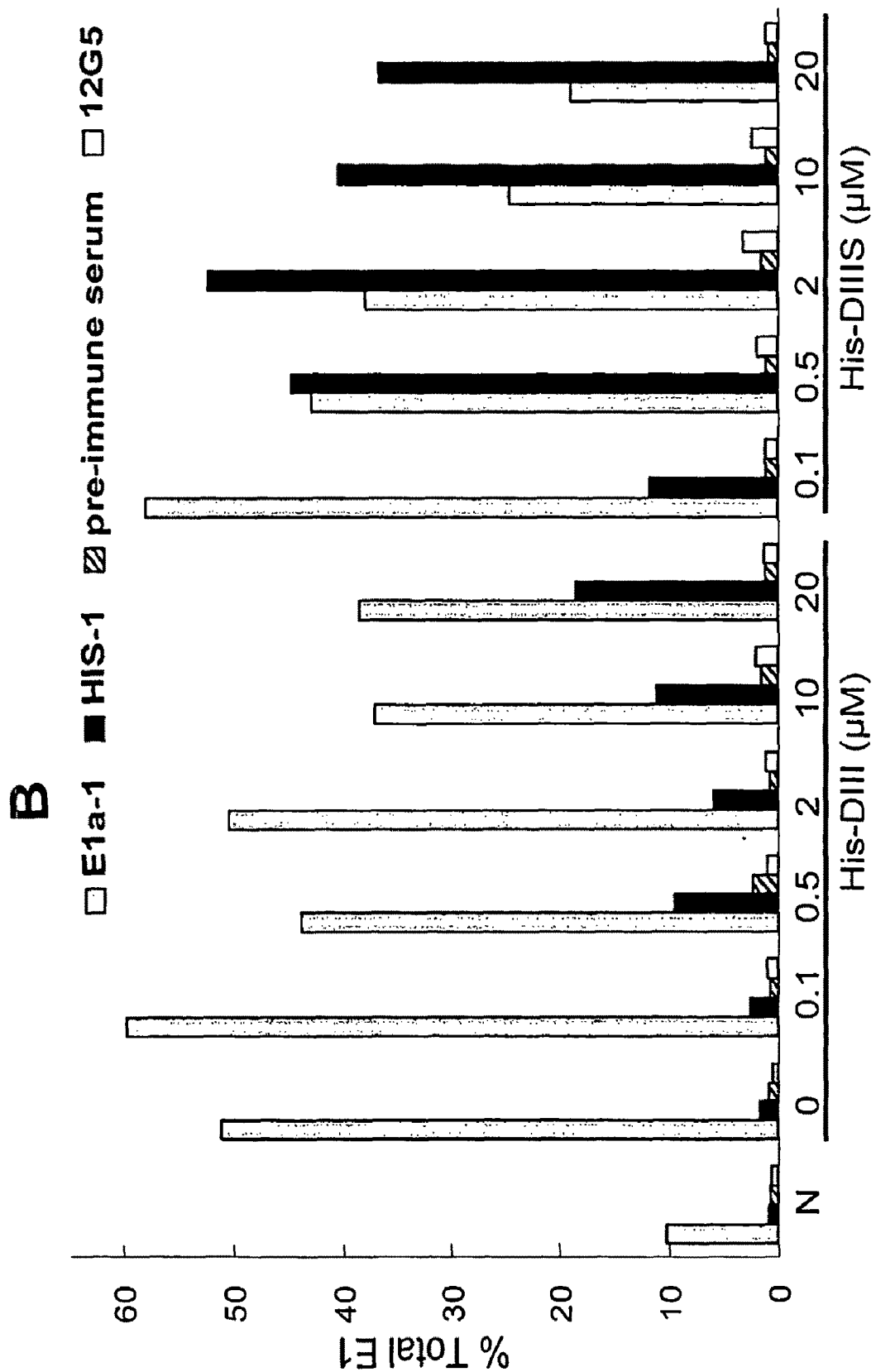
Figure 11C:
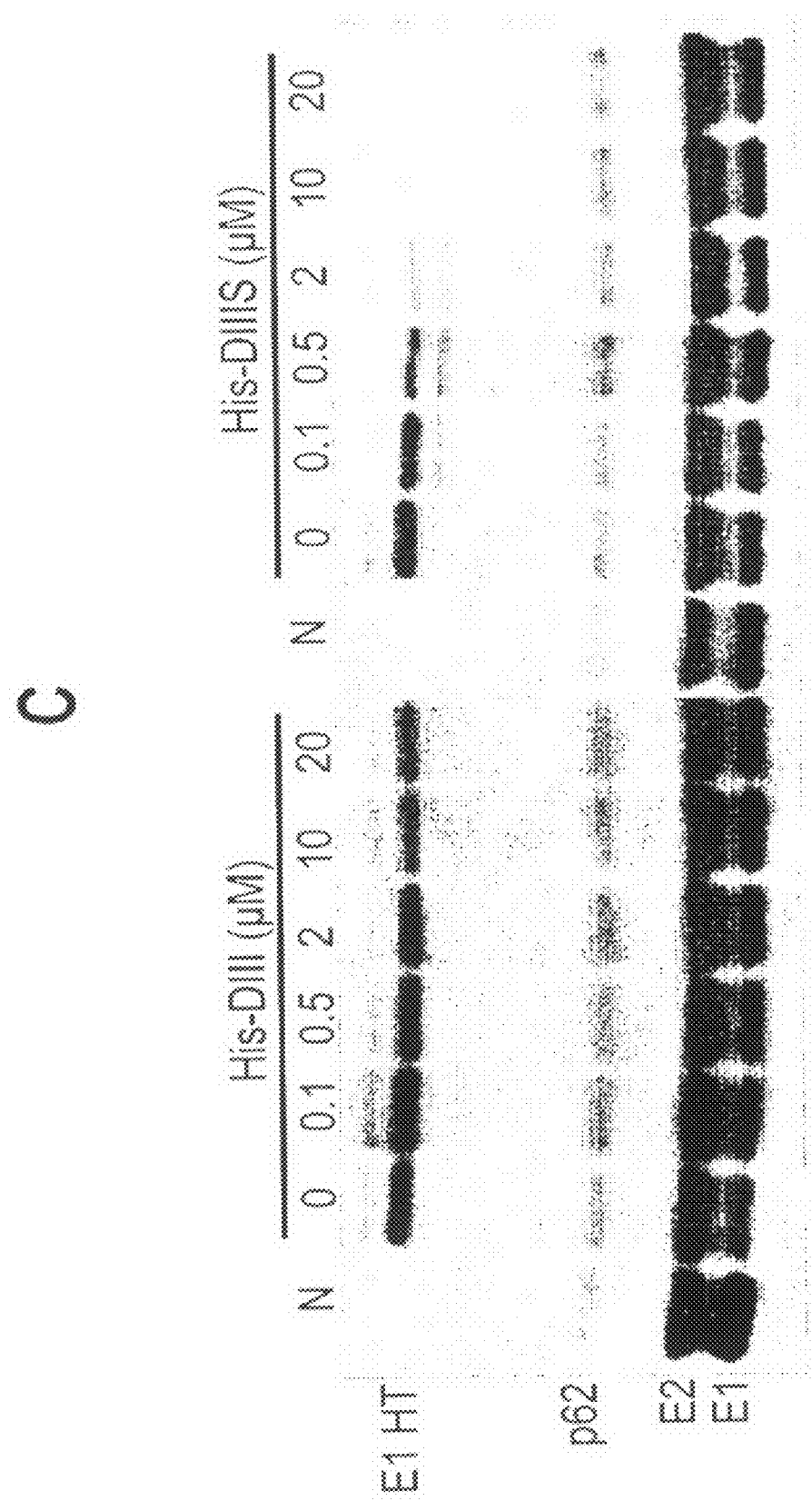

Quantitative analysis showed that the amount of E1 retrieved by the anti-His tag antibody increased when increasing amounts of domain III were present during the low pH step (FIG. 11B). His-DIII interaction retrieved about 18% of the total E1 at a concentration of 20 µM. Retrieval by His-DIIIS was maximal at 2 µM and ~50% of the total E1, similar to the amount of E1 that converted to reactivity with the acid-specific antibody. Interestingly, concentrations of His-DIIIS above 2 µM led to a gradual decrease in the retrieval of E1 by both the anti-His antibody and the acid-conformation specific antibody. This is the result that would be predicted if the presence of a high concentration of His-DIIIS is directly affecting the HT. We evaluated this possibility by quantitating the E1 HT band in SDS-PAGE, taking advantage of its relative resistance to dissociation by SDS sample buffer at 30° C. (FIG. 11C). Increasing amounts of His-DIIIS lead to the loss of the HT band, with only 10% of the control HT observed in the presence of 20 µM His-DIIIS. Thus, the presence of His-DIIIS interferes with the formation or stability of the E1 HT. Interestingly, addition of His-DIIIS produced bands migrating above and below the position of the HT, suggesting the presence of alternative E1 complexes (FIG. 11C). A decrease in the amount of E1HT was also observed in the presence of increasing amounts of His-DIII (60% of control HT at 20 μM His-DIII).

Figure 11D:
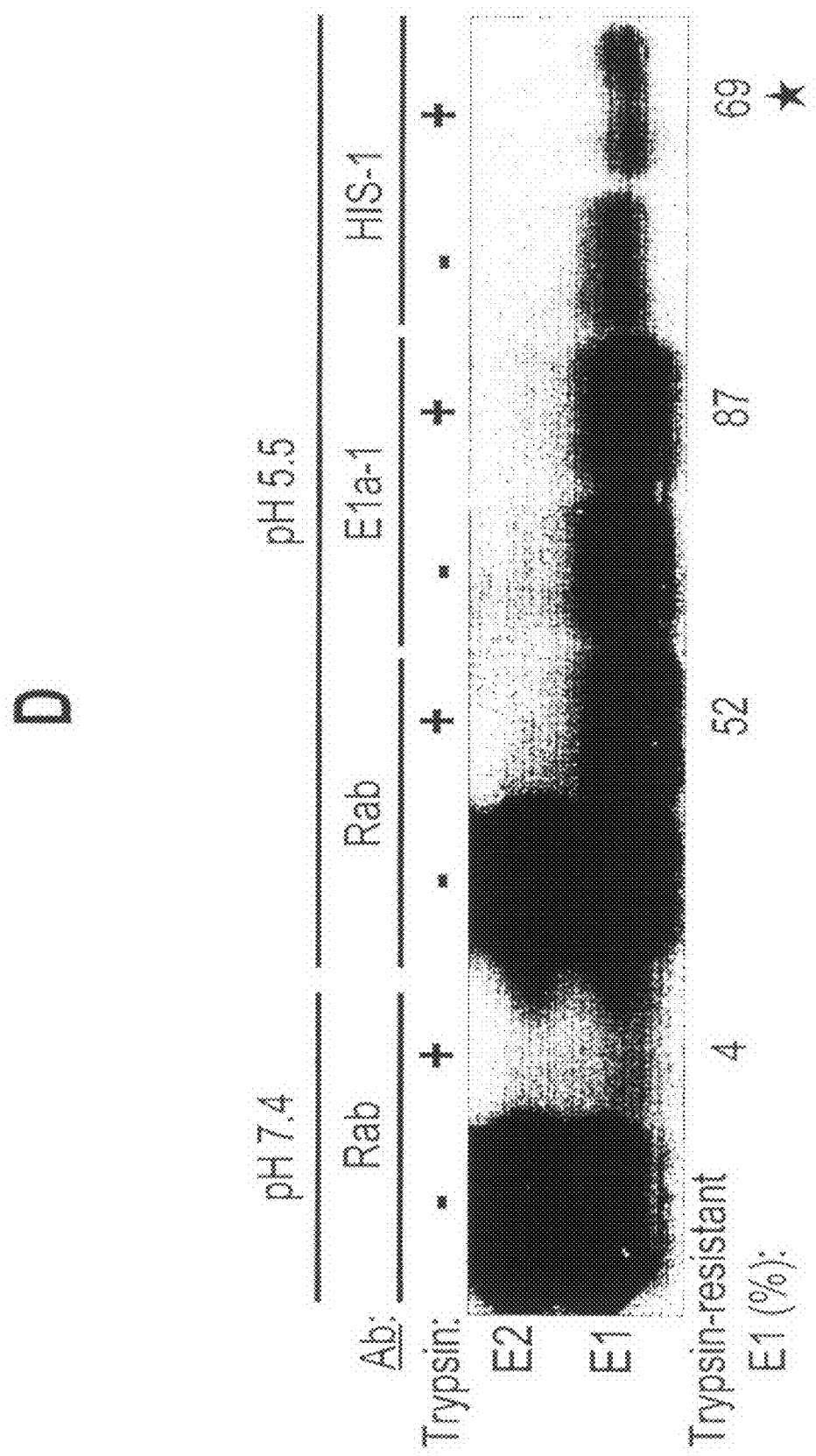

The target for domain III binding on E1 could be either the E1 monomer prior to trimerization, or a trimeric form of E1. A general property of trimeric E1 is its relative resistance to trypsin digestion, which is maintained even for E1 mutants that do not produce an SDS-resistant HT (Chatterjee et al., 2002). We treated cell-bound radiolabeled SFV at pH 7.4 or pH 5.5 in the presence of 10 μM His-DIII and used trypsin digestion to quantitate the amount of retrieved E1 trimer (FIG. 11D). About 50% of the total E1 converted to a trypsin-resistant trimer conformation following the low pH pulse. The E1 population retrieved by either E1a-1 or the antibody to the His-tag was strongly enriched in trypsin-resistant E1. Thus, domain III preferentially interacts with a trimeric conformation of E1, supporting a model in which the initial trimerization of E1 produces a binding site for exogenous domain III.

Discussion

We here demonstrate that exogenously added domain III can inhibit the alphavirus and flavivirus membrane fusion reactions. This is the first demonstration of such dominant-negative inhibition of the class II fusion proteins. Studies of class I inhibition by dominant-negative peptides such as T20 indicate that the speed of the fusion reaction controls its sensitivity to inhibition. Both the alphavirus and flavivirus fusion reactions are very rapidly triggered by low pH, with kinetics considerably faster than those of HIV-1, the target for T20. Nonetheless, domain III is able to inhibit the class II fusion reaction at the cell surface and within the normal endosomal entry pathway. Domain III inhibition thus provides proof of principle of a dominant-negative inhibitor strategy for the class II fusion proteins, and demonstrates the key role of the class II trimer in virus fusion and infection.

Our studies with SFV demonstrate that fusion is blocked at an early step prior to lipid mixing, and that domain III stably interacts with a trimeric form of E1. Unlike the E1 monomer, this E1 trimer contains a binding site for domain III, presumably comprised of the domain III/domain II "core trimer" with which domain III has been shown to interact in the 3-D structure of the homotrimer (Gibbons et al, 2004b). Thus domain III inhibition identifies an important intermediate state in the fusion reaction, which we interpret as reflecting formation of the core E1 trimer prior to the folding-back of E1 domain III. Our results indicate that this foldback step is required for lipid mixing as well as for full fusion. Given that the E1 fusion loop inserts in the target membrane prior to trimerization (Kielian et al, 1996), we assume that the domain III-sensitive state occurs after membrane insertion, but further studies will be needed to conclusively demonstrate this.

There are two populations of E1 homotrimers on the virus particles during fusion, HTs that interact with the target membrane and HTs outside the fusion site that probably insert into the virus membrane. Interestingly, the concentrations of His-DIIIS required to inhibit SFV fusion in the FIA are lower than those that maximally inhibit HT formation under the same conditions. This suggests that a subset of homotrimers is the critical target for fusion inhibition, and that this relatively small number of trimers would initially be affected, prior to disruption of the bulk E1 trimers. We favor a model in which domain III is blocking the fold-back of critical E1 trimers at the fusion site where the virus and target membranes are in close proximity. While our data do not rule out effects on E1 molecules outside the fusion zone, they do suggest that inhibition is unlikely to occur by completely blocking bulk HT formation.

Studies of the membrane insertion of class II fusion protein ectodomains indicate that insertion is highly cooperative (Gibbons et al, 2003, Stiasny et al, 2004). In the case of SFV, ectodomain insertion produces rings of 5-6 trimers, reflecting the physical associations of the fusion loops and domain III regions of adjacent HTs (Gibbons, 2000b; Gibbons et al., 2003). These cooperative interactions produce a volcano-like assembly of E1 HTs that may help to induce membrane curvature at the fusion site. An alternative model for inhibition by domain III is that it acts to inhibit such cooperative HT-HT interactions during fusion. While we hypothesize that these inter-trimer interactions are important for fusion, we feel that the strongest model for the action of domain III is that it acts not to prevent interactions between adjacent HTs, but to inhibit the folding-back reaction within one E1 molecule. This agrees well with the ability of domain III to co-immunoprecipitate E1 in the presence of octyl-glucoside, a detergent that we previously found disrupted HT-HT interactions (Gibbons et al., 2003; Gibbons, 2004a). It also agrees with the increase in inhibition and co-immunoprecipitation that is observed when the stem is present on domain III, since no role for the stem in HT-HT interaction was observed in the previous studies. However, it is possible that domain III could be acting by some combination of these two models. For example, prevention of E1 refolding by binding of exogenous domain III could inhibit the ability of the viral domain III to interact with domain III on an adjacent trimer.

Given the speed of the SFV fusion reaction, it is perhaps surprising that exogenous domain III can compete with the endogenous domain III for binding to the core HT. Such an inter-molecular interaction of domain III would seem to be at a disadvantage compared with the intramolecular interaction of the E1 domain III. Several factors may help to explain this paradox. The movement of domain III in the full-length E1 may be constrained by its attachment to the virus membrane through the stem/anchor domains. Indeed, we found that domain III binding to the ectodomain trimer was not as efficient as binding to the full-length trimer (data not shown), in keeping with the loss of the membrane anchor constraint in the ectodomain. The structure of the E1 homotrimer also reveals that the linker region between domain I and domain III becomes highly extended during the movement of domain III towards the fusion loop (Gibbons 2004B). This could provide an additional constraint to E1 domain III movement, allowing the initial interaction of exogenous domain III with the trimer. This initial binding of domain III could act to orient the stem region for its interaction with the core trimer. In this model, the domain III interaction would be the key first step in inhibition, followed by the close and sequential "zipping up" of the stem along the body of the trimer. This model also fits with the findings that inhibition of the class I and SNARE fusion reactions is most effective when it targets the initial membrane distal hairpin interaction.

While domain III is a useful basic research tool, its inhibitory action has important implications for the development of more clinically useful inhibitors of the class II proteins. Inhibition by domain III was observed within a virus genus (SFV vs. Sindbis) but not between members of the alphavirus genus and the flavivirus genus (SFV vs. DV2). This result suggests that key amino acid contacts between domain III and the core HT are conserved among viruses of the same genus. Simple examination of the HT structure and location of conserved residues does not clearly identify these critical target sites. However, since exogenous domain III showed stable binding to a trimeric E1 target, this interaction could be used as a general screen for peptides or small molecules that would block domain III-trimer binding. Given the cross-inhibition by domain III, such screens could have the potential to identify broad-specificity small molecule inhibitors.

While the first class I inhibitors were peptides, more recently small molecules that target critical sites of interaction in the trimer of hairpins have also been shown to act as fusion inhibitors (Clanci et al., 2004). Thus, although perhaps affecting only a subset of the contacts involved in the domain III-core trimer interaction, small molecules could act as potent inhibitors of class II fusion with the potential to act from within endocytic compartments.

Experimental Procedures

Cells and viruses. BHK-21 cells and C6/36 mosquito cells were cultured as previously described (Phalen and Kielian, 1991). SFV was a well-characterized plaque-purified isolate (Vashishtha et al, 1998), SIN was derived from the infectious clone of Toto 1101, VSV expressing GFP (VSV-GFP) was a generous gift from Dr. John K. Rose, DV2 (strain New Guinea C) was kindly provided by Dr. Stacey L. Bartlett, and DV1 (strain Western Pacific) was obtained from Dr. Richard Stockert. SFV, SIN and VSV-GFP were propagated in BHK-21 cells, while dengue viruses were propagated in C6/36 cells in DME containing 2% heat-inactivated FCS and 10 mM HEPES (pH 8.0).

Construction of domain III protein expression plasmids. DNA sequences of SFV E1 domain III (with or without stem region) were amplified from plasmid DG-1, and the DNA sequences of DV2 E domain III were obtained by RT-PCR on viral RNA extracted from DV2-infected C6/36 cells. These sequences were subcloned into protein expression plasmid pET-14b (Novogen) to express the exact domain III proteins with only one extra initiator methionine, and were also subcloned into pRSET A plasmid (Invitrogen) to express N-terminal 6× Histidine tagged domain III proteins with extra N-terminal 36 amino acids (aa). The DNA fragments subcloned into expression vectors were confirmed by DNA sequencing (Genewiz). Sequences of several of the proteins described herein are provided as SEQ ID NO:4-9.

Protein expression, refolding purification and concentration. Domain III proteins were expressed and refolded essentially as described in Zhang et al, 2002b. *E. coli* strain BL21 (DE3) competent cells (Novagen) were transformed with domain III protein expression plasmids, and cultured in Luria-Bertani (LB) medium with 50 μg/ml carbenicillin until $OD_{600}$ reached 0.6. Protein expression was then induced with 1 mM isopropylthiogalactosidase (IPTG) at 37° C. for 3 h. The cells were harvested by centrifuge, resuspended in lysis buffer (10 mM Tris, 150 mM NaCl, 25% (w/v) sucrose, 1 mM EDTA and 10 mM DTT, pH 8.0), supplemented with 0.1 mg/ml lysozyme, and frozen at −80° C. over night prior to be broken up by sonication. The insoluble inclusion body (IB) was collected by centrifuge at 20,000×g for 15 min, and washed 3 times with washing buffer (10 mM Tris, 100 mM NaCl, 1 mM EDTA and 10 mM DTT, pH 8.0) with 0.5% Triton X-100 and then 2 times with the same washing buffer without detergent. The washed inclusion body (IB) was solubilized in IB dilution buffer (6M guanidine-HCl, 10 mM NaAc and 5 mM EDTA, pH 4.6) with 1 mM DTT, and the protein concentration was determined by $OD_{280}$ using theoretically calculated extinction coefficient. In order to refold the denatured protein, 16 mg IB in 16 ml IB dilution buffer was quickly diluted into 1 L refolding buffer (100 mM Tris, 0.4 M arginine-HCl, 1 mM EDTA, 5 mM cysteamine, 0.5 mM cystamine and 0.5 mM phenylmethanesulfonylfluoride [PMSF], pH 8.5), and sat at 4° C. for 6-8 h before the next IB addition. There are about 5 IB dilutions in each protein preparation. The refolded proteins were concentrated from 1 L to 10 ml using an Amicon stirred ultrafiltration cell, loaded on Superdex G-75 gel filtration column (Amersham Biosciences), and eluted with elution buffer (10 mM Tris, 50 mM NaCl, pH 8.0). The correctly refolded protein was separated from aggregates and collected prior to concentration and buffer exchange to low salt buffer (10 mM Tris, 100 μM NaCl, pH 7.4) by 5000 molecular weight cutoff Vivaspin concentrator (Vivascience).

The concentration of domain III proteins was determined by absorption at 205 nm as described in Scopes, 1974. About 10 mg of dIII was produced from 100 mg of inclusion bodies purified from 1 liter of bacterial culture.

Sodium dodecyl sulfate-polyacrylamide gel electrophoresis (SDS-PAGE). Protein samples were heated in SDS sample buffer (200 mM Tris, 4% SDS, 10% glycerol, 0.02% bromophenol blue, pH 8.8) with or without 10 mM DTT at 95° C. or 30° C. for 3 min, and the alkylation was achieved by incubating with 30 mM iodoacetamide at 37° C. for 15 min. The processed protein samples were then loaded and electrophoresed on SDS-acrylamide gel with standard Tris-glycine system, except in FIG. 6B where a Tris-tricine system was used. $^{35}S$-labeled proteins were quantified by PhosphorImager analysis with Image Quant version 1.2 software (Molecular Dynamics, Sunnyvale, Calif.).

Mass spectrometry. Domain III proteins were measured by ESI mass spectrometry on a ThermoFinnigan LCQ ion trap mass spectrometer.

Fusion infection assay (FIA). Fusion of virus with the plasma membrane of BHK cells was assayed in FIA as previous described (Vashishtha et al, 1998). SFV, SIN and VSV-GFP were diluted in binding medium at pH 6.8 (RPMI without bicarbonate plus 0.2% BSA and 10 mM HEPES [RPMI/BSA/HEPES]) supplemented with 20 mM MES and 20 mM $NH_4Cl$), while dengue viruses were diluted in binding medium at pH 7.9 (RPMI/BSA/HEPES plus 20 mM $NH_4Cl$). BHK cells grown on 12-mm coverslips in 24-well plate were chilled on ice and washed twice with ice cold binding medium prior to binding with virus on ice for 90 to 120 min with gentle shaking (binding step). After virus binding, cells were washed 2 times with binding medium to get rid of unbound virus. The virus-cell membrane fusion was induced at 37° C. for 1 min in 200 μl pH medium (RPMI/BSA/HEPES plus 30 mM MES for pH 7.4 or RPMI/BSA/HEPES plus 30 mM sodium succinate for pH 6.0 or lower) (fusion step). Cells were put back on ice and washed 2 times with binding medium. SFV, SIN and VSV-GFP infected BHK cells were incubated at 28° C. overnight in BHK growth medium plus 20 mM $NH_4Cl$, while dengue viruses infected cells were incubated in Medium S (minimum essential medium [MEM] supplemented with 2% FCS) with 50 mM $NH_4Cl$ for 3 h at 37° C. prior to growth at 37° C. for 2 days in Medium S plus 20 mM $NH_4Cl$ (culture step).

Compared to SFV and SIN, dengue viruses started fusion at higher pH (~7) in FIA. DV2 and DV1 showed ~50% fusion at pH 6.5, and reached maximal fusion when fusion pH was lowered to 6.2, where the fusion efficiency of pre-bound dengue viruses was 30%.

Immunofluorescence microscopy. VSV-GFP infected cells were fixed in 3% formaldehyde at room temperature for 20 min, and VSV infected cells expressing GFP were observed directly without antibody staining under fluorescence microscopy. The cells infected by all other viruses were fixed in ice-cold methanol for 10 min. SFV and SIN infected cells were stained with rabbit polyclonal antisera against SFV or SIN, and then detected by FITC-conjugated goat anti-rabbit antibody. DV2 and DV1 infected cells were stained with mouse polyclonal hyperimmune ascites fluid against DV2 (obtained from Dr. Robert B. Tesh), and then detected by Alexa fluor 488 conjugated anti-mouse antibody (Molecular Probe). For each sample duplicate coverslips were evaluated at an infection level of >200 cells/coverslip in the absence of inhibitor.

Assays for SFV E1 homotrimer formation with domain III proteins. To assess the conformational change of SFV E1 protein during fusion in the presence of domain III proteins, the 35S-labeled SFV was generated as described before, and the fusion between $^{35}$S-labeled SFV and BHK cells were assayed as FIA. Immediately after the fusion step, the cells were lysed in lysis buffer (20 mM Tris, 100 mM NaCl, 1.5% octyl-glucoside, 1 mM EDTA, pH 7.4 plus 1 µg/ml pepstatin, 50 µg/ml leupeptin, 0.1% BSA, 100 µg/ml aprotitin and 1 mM PMSF). In order to assay the SDS resistant E1 homotrimer, one aliquot of lysates was added to SDS sample buffer and heated to 30° C. for 3 min prior to SDS-acrylamide 7% gel. Another aliquot of cell lysates was subjected to immunoprecipitation as previously described using different antibodies as indicated in FIG. 11, and the E1 protein bound to specific antibody was quantified after resolved in SDS-PAGE on 11% gel.

To further test the trypsin resistance of the immunoprecipitated E1 proteins, the immunoprecipitated pellets were resuspended in PBS with 1% TX-100, and were added to 1 mg/ml trypsin (freshly made in PBS/1% TX-100) to a final concentration of 125 µg/ml. The trypsin digestion was at 37° C. for 1 h and then stopped by adding 5 mM PMSF. These mixtures were added with SDS (final concentration as 2%), heated at 95° C. for 3 min, and shaken vigorously at room temperature for 4 min, then repeated twice. The insoluble zysorbin was spun away, and the supernatants were collected, precipitated in 1% TCA, washed in ice-cold acetone and subjected to SDS-PAGE.

Pyrene-labeled SFV fusion with cell membrane. Pyrene-labeled SFV was prepared as described before, and fused with BHK cell membrane essentially the same as FIA. In brief, BHK cells grown on 35 mm plates were pre-bound with pyrene-labeled SFV (diluted in binding medium [pH 6.8]) (MOI ~2000) by incubation on ice for 120 min with gentle shaking. Unbound virus was washed away, and the virus fusion on plasma membrane was induced at 37° C. for 1 min in pH 7.4 or pH 5.5 medium with certain concentrations of domain III proteins. Cells were put back on ice, washed once with binding medium, once with H—H solution (Hank's balanced salt solution buffered with 10 mM HEPES, pH 7.4 and supplemented with 20 mM NH$_4$Cl). The cells were then scraped off in H—H solution, transferred to a quartz cuvette, and pre-equilibrated in an AB-2 fluorometer for 1 min prior to the fluorescence scanning at 37° C. The cells bound with pyrene-labeled SFV were excited at 343 nm, and the fluorescence emission from 360 to 560 nm was recorded as average from 2 serial scanning. The fluorescence signal from empty cells was subtracted from each sample. The monomer pyrene fluorescence peak (M) is at 397 nm, while the concentrated pyrene probes originally in the viral membrane shows an eximer peak (Ex) at 475 nm. The lipid mixing between pyrene-labeled SFV and the target cells can be followed by the decrease of Ex/M ratio, i.e. the dilution of pyrene from viral membrane to cell plasma membrane.

Viral infection via regular endocytosis. SFV, SIN, VSV-GFP and DV2 were diluted in RPMI/BSA/HEPES (pH 7.2), mixed with various concentrations of domain III proteins, and seeded on BHK cells grown on 12-mm coverslips in 24-well plates. The cells were kept in a 20° C. water bath for 1 h to allow the regular virus infection via endocytosis. The infection was stopped by addition of growth medium plus NH$_4$Cl as in the culture step of FIA.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

SEQ ID NO:s

```
A Domain III of a class II fusion protein of a Semliki Forest Virus
                                                    SEQ ID NO: 1
VEAPTIIDLTCTVATCTHSSDFGGVLTLTYKTDKNGDCSVHSHSNVATLQEATAKVKTA
GKVTLHFSTASASPSFVVSLCSARATCSASCEPP A stem region of a class II fusion protein of a Semliki Forest Virus
                                                    SEQ ID NO: 2
KDHIVPYAASHSNVVFPDMSGTALSWVQK GenBank accession NP_819008: a class II fusion protein from a Semliki
Forest Virus (E protein). Domain III is in bold, the stem region is
in italics, and the Domain I/Domain III linker is underlined.
                                                    SEQ ID NO: 3
   1 yehstvmpnv vgfpykahie rpgyspltlq mqvvetslep tlnleyitce yktvvpspyv 61 kccgasecst kekpdyqckv ytgvypfmwg gaycfcdsen tqlseayvdr sdvcrhdhas 121 aykahtaslk akvrvmygnv nqtvdvyvng dhavtiggtq fifgplssaw tpfdnkivvy 181 kdevfnqdfp pygsgqpgrf gdiqsrtves ndlyantalk larpspgmvh vpytqtpsgf 241 kywlkekgta lntkapfgcq iktnpvramn cavgnipvsm nlpdsaftri veaptiidlt 301 ctvatcthss dfggvltlty ktkngdcsv hshsnvatlq eatakvktag kvtlhfstas 361 aspsfvvslc saratcsasc eppkdhivpy aashsnvvfp dmsgtalswv qkisgglgaf
```

-continued 421 aigailvlvv vtciglrr

SEQ ID NO: 4-7 Domain III proteins derived from a Semliki Forest Virus
E protein. See Example for nomenclature.

DIII
 SEQ ID NO: 4
MVEAPTIIDLTCTVATCTHSSDFGGVLTLTYKTDKNGDCSVHSHSNVATLQEATAKVKT
AGKVTLHFSTASASPSFVVSLCSARATCSASCEPP (Met + 291-383)

DIIIS
 SEQ ID NO: 5
MVEAPTIIDLTCTVATCTHSSDFGGVLTLTYKTDKNGDCSVHSHSNVATLQEATAKVKT
AGKVTLHFSTASASPSFVVSLCSARATCSASCEPPKDHIVPYAASHSNVVFPDMSGTALS
WVQK (Met + 291-412)

His-DIII
 SEQ ID NO: 6
MRGSHHHHHHGMASMTGGQQMGRDLYDDDDKDRWGSVEAPTIIDLTCTVATCTHSSD
FGGVLTLTYKTDKNGDCSVHSHSNVATLQEATAKVKTAGKVTLHFSTASASPSFVVSLC
SARATCSASCEPP (6-His tag underlined + 291-383)

His-DIIIS
 SEQ ID NO: 7
MRGSHHHHHHGMASMTGGQQMGRDLYDDDDKDRWGSVEAPTIIDLTCTVATCTHSSD
FGGVLTLTYKTDKNGDCSVHSHSNVATLQEATAKVKTAGKVTLHFSTASASPSFVVSLC
SARATCSASCEPPKDHIVPYAASHSNVVFPDMSGTALSWVQK (6-His tag underlined +
291-412)

SEQ ID NO: 8 and 9 Domain III proteins from Denaue virus 2 E.
See Example for nomenclature.

DV2DIIIH1
 SEQ ID NO: 8
MGMSYSMCTGKFKVVKEIAETQHGTIVIRVQYEGDGSPCKIPPFEIMDLEKRHVLGRLITV
NPIVTEKDSPVNIEAEPPFGDSYIIIGVEPGQLKLNWFKKGSSIGQMIETTMRGAKRMAIL
(Met + 296-395 + H1 396-415)

His-DV2DIII
 SEQ ID NO: 9
MRGSHHHHHHGMASMTGGQQMGRDLYDDDDKDRWGSGMSYSMCTGKFKVVKEIAE
TQHGTIVIRVQYEGDGSPCKIPPFEIMDLEKRHVLGRLITVNPIVTEKDSPVNIEAEPPFGDS
YIIIGVEPGQLKLNWFKKG (6-His tag underlined + 296-395)

A Domain III of a class II fusion protein of a Semliki Forest
Virus with the DI/DIII linker
 SEQ ID NO: 10
MNLPDSAFTRIVEAPTIIDLTCTVATCTHSSDFGGVLTLTYKTDKNGDCSVHSNVATL
QEATAKVKTAGKVTLHFSTASASPSFVVSLCSARATCSASCEPP A DI/DIII linker from a class II fusion protein of a Semliki
Forest Virus
 SEQ ID NO: 11
MNLPDSAFTRI

---

What is claimed is:

1. A method of screening a test compound for the ability to inhibit infection by a virus having a class II viral fusion protein, the method comprising:
   (a) combining the test compound with
      (i) an aqueous-soluble protein comprising a domain having the sequence set forth in SEQ ID NO:1, and
      (ii) a core homotrimer of the class II viral fusion protein; and
   (b) quantitating binding of the aqueous-soluble protein to the core homotrimer,
   wherein reduced binding of the aqueous-soluble protein to the core homotrimer in the presence of the test compound as compared to binding of the aqueous-soluble protein to the core homotrimer in the absence of the test compound indicates that the test compound inhibits infection by the virus having the class II viral fusion protein.

2. The method of claim 1, wherein the aqueous-soluble protein further comprises at least a portion of a stem region of an Alphavirus fusion protein, wherein the stem region comprises SEQ ID NO:2.

3. The method of claim 1, wherein the aqueous-soluble protein further comprises a DI/DIII linker region from an Alphavirus class II fusion protein, wherein the Alphavirus linker region has SEQ ID NO: 11.

4. The method of claim 1, wherein the aqueous-soluble protein further comprises an oligohistidine moiety.

5. The method of claim 1, wherein the aqueous-soluble protein is labeled with a detectable label.

6. The method of claim 5, wherein the detectable label is a fluorescent molecule, a radioactive atom, an enzyme, or an antigen not naturally occurring in the aqueous-soluble protein.

7. The method of claim 5, wherein the detectable label is a fluorescent molecule.

8. The method of claim 7, wherein quantitating binding of the aqueous-soluble protein and the core homotrimer in step b) is performed by fluorescence polarization.

9. The method of claim 7, wherein quantitating binding of the aqueous-soluble protein and the core homotrimer in step b) is performed by fluorescence resonance energy transfer.

10. The method of claim 1, wherein the core homotrimer does not comprise a Domain III of an Alphavirus fusion protein.

11. The method of claim 1, wherein the core homotrimer is immobilized on a solid matrix.

12. The method of claim 1, wherein the aqueous-soluble protein is immobilized on a solid matrix.

\* \* \* \*

SEQUENCE LISTING

<160> NUMBER OF SEQ ID NOS: 11

<210> SEQ ID NO 1
<211> LENGTH: 93
<212> TYPE: PRT
<213> ORGANISM: artificial
<220> FEATURE:
<223> OTHER INFORMATION: Domain III of a class II fusion protein of a
  Semliki Forest Virus

<400> SEQUENCE: 1

Val Glu Ala Pro Thr Ile Ile Asp Leu Thr Cys Thr Val Ala Thr Cys
1      5        10        15

Thr His Ser Ser Asp Phe Gly Gly Val Leu Thr Leu Thr Tyr Lys Thr
      20        25        30

Asp Lys Asn Gly Asp Cys Ser Val His Ser His Ser Asn Val Ala Thr
    35        40        45

```
Leu Gln Glu Ala Thr Ala Lys Val Lys Thr Ala Gly Lys Val Thr Leu
     50                  55                  60

His Phe Ser Thr Ala Ser Ala Ser Pro Ser Phe Val Val Ser Leu Cys
 65                  70                  75                  80

Ser Ala Arg Ala Thr Cys Ser Ala Ser Cys Glu Pro Pro
                 85                  90

<210> SEQ ID NO 2
<211> LENGTH: 29
<212> TYPE: PRT
<213> ORGANISM: artificial
<220> FEATURE:
<223> OTHER INFORMATION: Stem region of a class II fusion protein of a
      Semliki Forest Virus

<400> SEQUENCE: 2

Lys Asp His Ile Val Pro Tyr Ala Ala Ser His Ser Asn Val Val Phe
 1               5                  10                  15

Pro Asp Met Ser Gly Thr Ala Leu Ser Trp Val Gln Lys
             20                  25

<210> SEQ ID NO 3
<211> LENGTH: 438
<212> TYPE: PRT
<213> ORGANISM: artificial
<220> FEATURE:
<223> OTHER INFORMATION: Class II fusion protein from a Semliki Forest
      Virus (E protein)

<400> SEQUENCE: 3

Tyr Glu His Ser Thr Val Met Pro Asn Val Val Gly Phe Pro Tyr Lys
 1               5                  10                  15

Ala His Ile Glu Arg Pro Gly Tyr Ser Pro Leu Thr Leu Gln Met Gln
             20                  25                  30

Val Val Glu Thr Ser Leu Glu Pro Thr Leu Asn Leu Glu Tyr Ile Thr
         35                  40                  45

Cys Glu Tyr Lys Thr Val Val Pro Ser Pro Tyr Val Lys Cys Cys Gly
     50                  55                  60

Ala Ser Glu Cys Ser Thr Lys Glu Lys Pro Asp Tyr Gln Cys Lys Val
 65                  70                  75                  80

Tyr Thr Gly Val Tyr Pro Phe Met Trp Gly Gly Ala Tyr Cys Phe Cys
                 85                  90                  95

Asp Ser Glu Asn Thr Gln Leu Ser Glu Ala Tyr Val Asp Arg Ser Asp
             100                 105                 110

Val Cys Arg His Asp His Ala Ser Ala Tyr Lys Ala His Thr Ala Ser
         115                 120                 125

Leu Lys Ala Lys Val Arg Val Met Tyr Gly Asn Val Asn Gln Thr Val
    130                 135                 140

Asp Val Tyr Val Asn Gly Asp His Ala Val Thr Ile Gly Gly Thr Gln
145                 150                 155                 160

Phe Ile Phe Gly Pro Leu Ser Ser Ala Trp Thr Pro Phe Asp Asn Lys
                165                 170                 175

Ile Val Val Tyr Lys Asp Glu Val Phe Asn Gln Asp Phe Pro Pro Tyr
            180                 185                 190

Gly Ser Gly Gln Pro Gly Arg Phe Gly Asp Ile Gln Ser Arg Thr Val
        195                 200                 205

Glu Ser Asn Asp Leu Tyr Ala Asn Thr Ala Leu Lys Leu Ala Arg Pro
    210                 215                 220

Ser Pro Gly Met Val His Val Pro Tyr Thr Gln Thr Pro Ser Gly Phe
```

```
                    225                 230                 235                 240

Lys Tyr Trp Leu Lys Glu Lys Gly Thr Ala Leu Asn Thr Lys Ala Pro
                245                 250                 255

Phe Gly Cys Gln Ile Lys Thr Asn Pro Val Arg Ala Met Asn Cys Ala
            260                 265                 270

Val Gly Asn Ile Pro Val Ser Met Asn Leu Pro Asp Ser Ala Phe Thr
        275                 280                 285

Arg Ile Val Glu Ala Pro Thr Ile Ile Asp Leu Thr Cys Thr Val Ala
    290                 295                 300

Thr Cys Thr His Ser Ser Asp Phe Gly Gly Val Leu Thr Leu Thr Tyr
305                 310                 315                 320

Lys Thr Asn Lys Asn Gly Asp Cys Ser Val His Ser His Ser Asn Val
                325                 330                 335

Ala Thr Leu Gln Glu Ala Thr Ala Lys Val Lys Thr Ala Gly Lys Val
            340                 345                 350

Thr Leu His Phe Ser Thr Ala Ser Ala Ser Pro Ser Phe Val Val Ser
        355                 360                 365

Leu Cys Ser Ala Arg Ala Thr Cys Ser Ala Ser Cys Glu Pro Pro Lys
    370                 375                 380

Asp His Ile Val Pro Tyr Ala Ala Ser His Ser Asn Val Val Phe Pro
385                 390                 395                 400

Asp Met Ser Gly Thr Ala Leu Ser Trp Val Gln Lys Ile Ser Gly Gly
                405                 410                 415

Leu Gly Ala Phe Ala Ile Gly Ala Ile Leu Val Leu Val Val Val Thr
            420                 425                 430

Cys Ile Gly Leu Arg Arg
        435

<210> SEQ ID NO 4
<211> LENGTH: 94
<212> TYPE: PRT
<213> ORGANISM: artificial
<220> FEATURE:
<223> OTHER INFORMATION: Domain III protein derived from a Semliki
      Forest Virus E protein

<400> SEQUENCE: 4

Met Val Glu Ala Pro Thr Ile Ile Asp Leu Thr Cys Thr Val Ala Thr
1               5                   10                  15

Cys Thr His Ser Ser Asp Phe Gly Gly Val Leu Thr Leu Thr Tyr Lys
            20                  25                  30

Thr Asp Lys Asn Gly Asp Cys Ser Val His Ser His Ser Asn Val Ala
        35                  40                  45

Thr Leu Gln Glu Ala Thr Ala Lys Val Lys Thr Ala Gly Lys Val Thr
    50                  55                  60

Leu His Phe Ser Thr Ala Ser Ala Ser Pro Ser Phe Val Val Ser Leu
65                  70                  75                  80

Cys Ser Ala Arg Ala Thr Cys Ser Ala Ser Cys Glu Pro Pro
                85                  90

<210> SEQ ID NO 5
<211> LENGTH: 123
<212> TYPE: PRT
<213> ORGANISM: artificial
<220> FEATURE:
<223> OTHER INFORMATION: Domain III protein derived from a Semliki
      Forest Virus E protein

<400> SEQUENCE: 5
```

```
Met Val Glu Ala Pro Thr Ile Ile Asp Leu Thr Cys Thr Val Ala Thr
1               5                   10                  15

Cys Thr His Ser Ser Asp Phe Gly Gly Val Leu Thr Leu Thr Tyr Lys
            20                  25                  30

Thr Asp Lys Asn Gly Asp Cys Ser Val His Ser His Ser Asn Val Ala
            35                  40                  45

Thr Leu Gln Glu Ala Thr Ala Lys Val Lys Thr Ala Gly Lys Val Thr
50                  55                  60

Leu His Phe Ser Thr Ala Ser Ala Ser Pro Ser Phe Val Val Ser Leu
65                  70                  75                  80

Cys Ser Ala Arg Ala Thr Cys Ser Ala Ser Cys Glu Pro Pro Lys Asp
                85                  90                  95

His Ile Val Pro Tyr Ala Ala Ser His Ser Asn Val Phe Pro Asp
            100                 105                 110

Met Ser Gly Thr Ala Leu Ser Trp Val Gln Lys
            115                 120
```

<210> SEQ ID NO 6
<211> LENGTH: 129
<212> TYPE: PRT
<213> ORGANISM: artificial
<220> FEATURE:
<223> OTHER INFORMATION: Domain III protein derived from a Semliki Forest Virus E protein

<400> SEQUENCE: 6

```
Met Arg Gly Ser His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Val Glu Ala Pro Thr Ile Ile Asp Leu Thr Cys Thr
            35                  40                  45

Val Ala Thr Cys Thr His Ser Ser Asp Phe Gly Gly Val Leu Thr Leu
50                  55                  60

Thr Tyr Lys Thr Asp Lys Asn Gly Asp Cys Ser Val His Ser His Ser
65                  70                  75                  80

Asn Val Ala Thr Leu Gln Glu Ala Thr Ala Lys Val Lys Thr Ala Gly
                85                  90                  95

Lys Val Thr Leu His Phe Ser Thr Ala Ser Ala Ser Pro Ser Phe Val
            100                 105                 110

Val Ser Leu Cys Ser Ala Arg Ala Thr Cys Ser Ala Ser Cys Glu Pro
            115                 120                 125

Pro
```

<210> SEQ ID NO 7
<211> LENGTH: 158
<212> TYPE: PRT
<213> ORGANISM: artificial
<220> FEATURE:
<223> OTHER INFORMATION: Domain III protein derived from a Semliki Forest Virus E protein

<400> SEQUENCE: 7

```
Met Arg Gly Ser His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Val Glu Ala Pro Thr Ile Ile Asp Leu Thr Cys Thr
```

```
                    35                  40                  45
Val Ala Thr Cys Thr His Ser Ser Asp Phe Gly Gly Val Leu Thr Leu
 50                  55                  60

Thr Tyr Lys Thr Asp Lys Asn Gly Asp Cys Ser Val His Ser His Ser
 65                  70                  75                  80

Asn Val Ala Thr Leu Gln Glu Ala Thr Ala Lys Val Lys Thr Ala Gly
                 85                  90                  95

Lys Val Thr Leu His Phe Ser Thr Ala Ser Ala Ser Pro Ser Phe Val
                100                 105                 110

Val Ser Leu Cys Ser Ala Arg Ala Thr Cys Ser Ala Ser Cys Glu Pro
                115                 120                 125

Pro Lys Asp His Ile Val Pro Tyr Ala Ala Ser His Ser Asn Val Val
                130                 135                 140

Phe Pro Asp Met Ser Gly Thr Ala Leu Ser Trp Val Gln Lys
145                 150                 155

<210> SEQ ID NO 8
<211> LENGTH: 121
<212> TYPE: PRT
<213> ORGANISM: artificial
<220> FEATURE:
<223> OTHER INFORMATION: Domain III protein derived from Dengue virus
      2 E

<400> SEQUENCE: 8

Met Gly Met Ser Tyr Ser Met Cys Thr Gly Lys Phe Lys Val Val Lys
 1               5                  10                  15

Glu Ile Ala Glu Thr Gln His Gly Thr Ile Val Ile Arg Val Gln Tyr
                20                  25                  30

Glu Gly Asp Gly Ser Pro Cys Lys Ile Pro Phe Glu Ile Met Asp Leu
             35                  40                  45

Glu Lys Arg His Val Leu Gly Arg Leu Ile Thr Val Asn Pro Ile Val
 50                  55                  60

Thr Glu Lys Asp Ser Pro Val Asn Ile Glu Ala Glu Pro Pro Phe Gly
 65                  70                  75                  80

Asp Ser Tyr Ile Ile Ile Gly Val Glu Pro Gly Gln Leu Lys Leu Asn
                85                  90                  95

Trp Phe Lys Lys Gly Ser Ser Ile Gly Gln Met Ile Glu Thr Thr Met
                100                 105                 110

Arg Gly Ala Lys Arg Met Ala Ile Leu
                115                 120

<210> SEQ ID NO 9
<211> LENGTH: 136
<212> TYPE: PRT
<213> ORGANISM: artificial
<220> FEATURE:
<223> OTHER INFORMATION: Domain III protein derived from Dengue virus
      2 E

<400> SEQUENCE: 9

Met Arg Gly Ser His His His His His His Gly Met Ala Ser Met Thr
 1               5                  10                  15

Gly Gly Gln Gln Met Gly Arg Asp Leu Tyr Asp Asp Asp Lys Asp
                20                  25                  30

Arg Trp Gly Ser Gly Met Ser Tyr Ser Met Cys Thr Gly Lys Phe Lys
             35                  40                  45

Val Val Lys Glu Ile Ala Glu Thr Gln His Gly Thr Ile Val Ile Arg
 50                  55                  60
```

```
Val Gln Tyr Glu Gly Asp Gly Ser Pro Cys Lys Ile Pro Phe Glu Ile
 65                  70                  75                  80

Met Asp Leu Glu Lys Arg His Val Leu Gly Arg Leu Ile Thr Val Asn
                 85                  90                  95

Pro Ile Val Thr Glu Lys Asp Ser Pro Val Asn Ile Glu Ala Glu Pro
                100                 105                 110

Pro Phe Gly Asp Ser Tyr Ile Ile Ile Gly Val Glu Pro Gly Gln Leu
            115                 120                 125

Lys Leu Asn Trp Phe Lys Lys Gly
    130                 135

<210> SEQ ID NO 10
<211> LENGTH: 104
<212> TYPE: PRT
<213> ORGANISM: artificial
<220> FEATURE:
<223> OTHER INFORMATION: Domain III of a class II fusion protein of a
      Semliki Forest Virus with the DI/DIII linker

<400> SEQUENCE: 10

Met Asn Leu Pro Asp Ser Ala Phe Thr Arg Ile Val Glu Ala Pro Thr
  1               5                  10                  15

Ile Ile Asp Leu Thr Cys Thr Val Ala Thr Cys Thr His Ser Ser Asp
                 20                  25                  30

Phe Gly Gly Val Leu Thr Leu Thr Tyr Lys Thr Asp Lys Asn Gly Asp
             35                  40                  45

Cys Ser Val His Ser His Ser Asn Val Ala Thr Leu Gln Glu Ala Thr
 50                  55                  60

Ala Lys Val Lys Thr Ala Gly Lys Val Thr Leu His Phe Ser Thr Ala
 65                  70                  75                  80

Ser Ala Ser Pro Ser Phe Val Val Ser Leu Cys Ser Ala Arg Ala Thr
                 85                  90                  95

Cys Ser Ala Ser Cys Glu Pro Pro
            100

<210> SEQ ID NO 11
<211> LENGTH: 11
<212> TYPE: PRT
<213> ORGANISM: artificial
<220> FEATURE:
<223> OTHER INFORMATION: DI/DIII linker from a class II fusion protein
      of a Semliki Forest Virus

<400> SEQUENCE: 11

Met Asn Leu Pro Asp Ser Ala Phe Thr Arg Ile
  1               5                  10
```